(12) United States Patent
Copik et al.

(10) Patent No.: US 11,617,781 B2
(45) Date of Patent: Apr. 4, 2023

(54) METHODS AND COMPOSITIONS FOR NATURAL KILLER CELLS

(71) Applicant: UNIVERSITY OF CENTRAL FLORIDA RESEARCH FOUNDATION, INC., Orlando, FL (US)

(72) Inventors: Alicja Copik, Casselberry, FL (US); Vijay Reddy, Orlando, FL (US); Jeremiah Oyer, Longwood, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 595 days.

(21) Appl. No.: 16/672,949

(22) Filed: Nov. 4, 2019

(65) Prior Publication Data
US 2020/0138908 A1 May 7, 2020

Related U.S. Application Data

(60) Division of application No. 15/489,460, filed on Apr. 17, 2017, now Pat. No. 10,463,715, which is a continuation of application No. 14/410,787, filed as application No. PCT/US2013/048678 on Jun. 28, 2013, now Pat. No. 9,623,082.

(60) Provisional application No. 61/665,591, filed on Jun. 28, 2012.

(51) Int. Cl.
*A61K 38/20* (2006.01)
*C12N 5/0783* (2010.01)
*A61K 38/17* (2006.01)

(52) U.S. Cl.
CPC .............. *A61K 38/20* (2013.01); *A61K 38/17* (2013.01); *C12N 5/0646* (2013.01); *C12N 2500/84* (2013.01); *C12N 2501/2315* (2013.01); *C12N 2501/2321* (2013.01); *C12N 2501/50* (2013.01); *C12N 2501/599* (2013.01)

(58) Field of Classification Search
None
See application file for complete search history.

(56) References Cited

U.S. PATENT DOCUMENTS

| | | | |
|---|---|---|---|
| 6,500,641 B1 | 12/2002 | Chen et al. | |
| 6,849,452 B1 | 2/2005 | Zitvogel et al. | |
| 7,435,596 B2 | 10/2008 | Campana et al. | |
| 8,026,097 B2 | 9/2011 | Campana et al. | |
| 2002/0114781 A1 | 8/2002 | Strom et al. | |
| 2003/0143191 A1 | 7/2003 | Bell et al. | |
| 2003/0148454 A1 | 8/2003 | Marshak-Rothstein | |
| 2006/0073591 A1 | 4/2006 | Abitorabi et al. | |
| 2006/0223769 A1 | 10/2006 | Dow et al. | |
| 2007/0031374 A1 | 2/2007 | Moller et al. | |
| 2007/0122413 A1 | 5/2007 | Sivakumar et al. | |
| 2007/0243159 A1 | 10/2007 | Selvaraj | |
| 2007/0292431 A1 | 12/2007 | Zheng et al. | |
| 2009/0104170 A1 | 4/2009 | Childs et al. | |
| 2010/0111916 A1 | 5/2010 | Kiang et al. | |
| 2010/0158936 A1 | 6/2010 | Shirwan et al. | |
| 2010/0272718 A1 | 10/2010 | Urso et al. | |
| 2012/0076790 A1 | 3/2012 | Classon et al. | |
| 2014/0234320 A1 | 8/2014 | Croft et al. | |
| 2015/0132254 A1 | 5/2015 | Wittrup et al. | |

FOREIGN PATENT DOCUMENTS

| WO | 2005018610 A1 | 3/2005 |
|---|---|---|
| WO | 2010071836 A1 | 6/2010 |
| WO | 2013175237 A1 | 11/2013 |

OTHER PUBLICATIONS

Anderson P M et al. "Cytokines in liposomes: Preliminary sudies with IL-1. IL-2, IL-6, GM-CSF and interferon-gamma", Cytokine, Academic Press Ltd, Philadelphia, PA, US, vol. 6 No. 1, Jan. 1, 1994, pp. 92-101.
Broekhoven Van C L et al: A novel approach for modifying tumor cell-derived plasma membrane vesicles to contain encapsulated IL-2 and engrafted costimulatory molecules for use in tumor immunotherapy, International Journal of Dancer, John Wiley & Sons, Inc. vol. 98, No. 1, Mar. 1, 2002, pp. 63-72.
Cecele J. Denman et al.: "Membrane-Cound IL-21 Promotes Sustained Ex Vivo Proliferation of Human Natural Killer Dells", PLOS ONE, vol. 7, No. 1, Jan. 18, 2012, p. e30264.
David A Christian et al.: "Particle-mediated delivery of cytokines for immunotherapy", Immunotherapy vol. 4, No. 4, Apr. 1, 2012, pp. 425-441.
Dominic A Colosimo: Multiple Aspects of Natural Killer Cell Expansion in Relevance to Immunotherapy for Hematologic Maligancies, Aug. 1, 2012.
Klempner M S et al: "Neutrophil plasma membranes. L High-ield purification of human neutrophil plasma membrane vesicles by nitrogen cavitation and differential centrifugation", The Journal of Cell Biology: JCB, The Rockefeller University Press, US, vol. 86. No. 1, Jul. 1, 1980, pp. 21-28.
Lachman L B et al: "Cytokine-containing liposomes as vaccine adjuvants." European Cytokine Network Dec. 1996, vol. 7, No. 4, Dec. 1996, pp. 693-698.
Dyer, Jeremiah L et al: "Generation of Highly Cytotoxic Natural Killer Cells for Treatment of Acute Myelogenous Leukemia Using a Feeder-Free, Particle-Based Approach", Biology of Blood and Marrow Transplantation, vol. 21, No. 4, Apr. 30, 2015, pp. 632-639.
Extended European Search Report issued in related European Application No. 13809630.0 dated Nov. 15, 2015.

(Continued)

*Primary Examiner* — Daniel C Gamett
(74) *Attorney, Agent, or Firm* — Meunier Carlin & Curfman LLC

(57) ABSTRACT

The application provides new compositions and methods for stimulating the production of natural killer (NK) cells in a subject. NK cells can be selectively expanded with a combination of stimulating ligands. Methods and compositions for the administration of stimulatory ligands modified to self-insert into tumor cells, thereby stimulating an increase in the number of NK cells in proximity to a tumor, are also described.

13 Claims, 18 Drawing Sheets

(56) References Cited

OTHER PUBLICATIONS

International Search Report and Written Opinion issued in related International Application No. PCT/US2013/048678 dated Nov. 29, 2013.
Denman et al., Membrane-Bound IL-21 Promotes Sustained Ex Vivo Proliferation of Human Natural Killer Cells, PLoS ONE, Jan. 2012, vol. 7:1, pp. 1-13.
Thery et al., Nature Reviews Immuno. 2009, vol. 9, 581-593.
Non-Final Office Action issued for U.S. Appl. No. 16/138,095, dated Jan. 17, 2020.

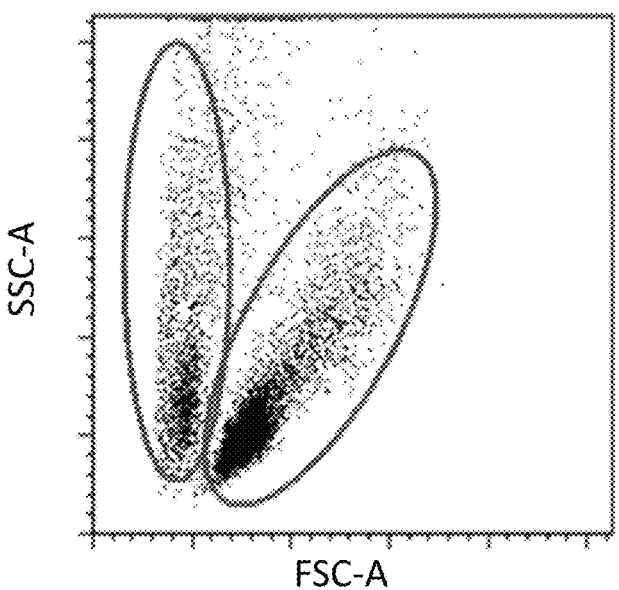
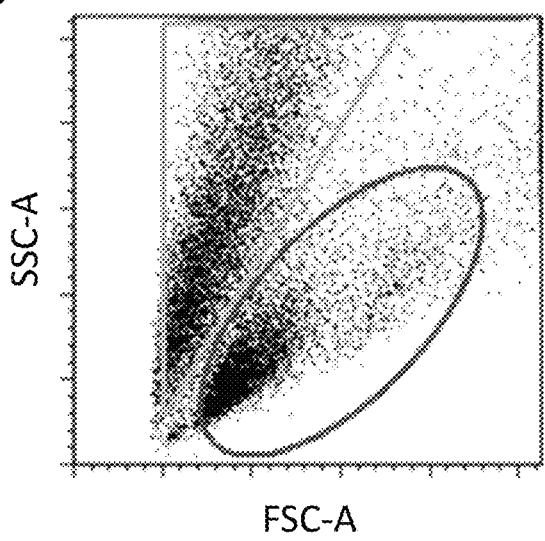
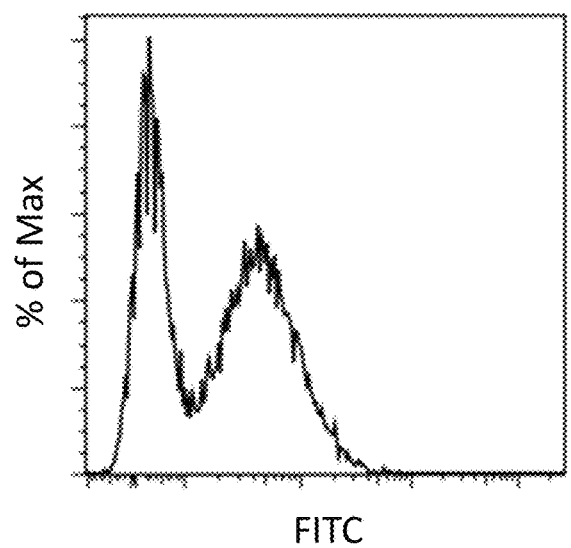
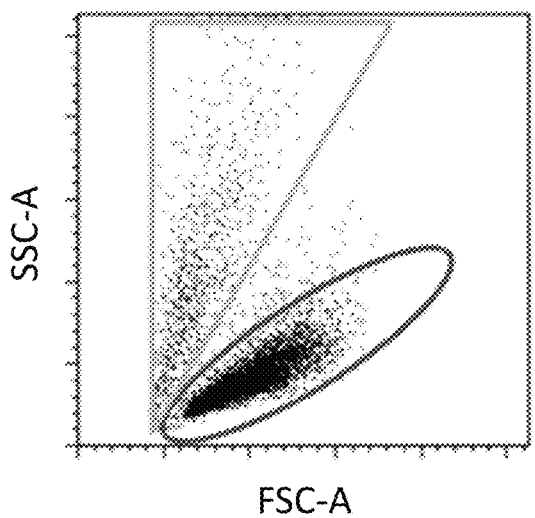
FIG. 8A and FIG. 8B

METHODS AND COMPOSITIONS FOR NATURAL KILLER CELLS

CROSS-REFERENCE TO RELATED APPLICATIONS

This application is a divisional of and claim priority to U.S. application Ser. No. 15/489,460, filed on Apr. 17, 2017, which is a continuation of and claims priority to U.S. application Ser. No. 14/410,787, filed Dec. 23, 2014, now U.S. Pat. No. 9,623,082, which is a 35 U.S.C. § 371 national stage application of PCT Application No. PCT/US2013/048678 filed on Jun. 28, 2013, which claims benefit of U.S. Provisional Application No. 61/665,591, filed Jun. 28, 2012, the disclosures of which are hereby incorporated herein by reference in their entireties.

FIELD OF THE INVENTION

The present application generally relates to compositions and methods comprising natural killer (NK) cells. More particularly, the application relates to the n vivo or in vitro stimulation and expansion of endogenous natural killer (NK) cells, which are capable of attacking and killing immune cells and cancer cells.

BACKGROUND

Hematopoietic stem cell transplantation (HSCT) from genotypically HLA-matched siblings has improved long-term survival in patients with hematologic cancer malignancies and marrow failure syndromes. Every year, more than 10,000 Americans get life-threatening diseases for which the only hope of a cure is a bone marrow transplant from an unrelated donor or cord blood unit. However, more than 70% of patients who could benefit from an allogeneic stem cell transplant do not have a matched sibling donor, (Henslee-Downey, et al. 1997). These circumstances delay treatment, making it necessary to resort to less than optimal use of a partially mismatched donor, which eventually leads to increased incidence of graft-versus-host disease (GVHD), graft failure, and relapse, all of which dramatically decrease patient survival (Drobyski, et al. 2002), (Baker, et al. 2009).

Additional limitations are posed by the duration and the costly financial, mental, and health burdens of the transplant process. Thus, the application of HSCT from an unrelated donor is limited to younger, healthier patients with appropriate socioeconomic support that can endure the process.

Further challenges are posed by the high rate of relapse due to the inability to eradicate residual cancer cells. Although HSCT is considered to be curative, cancer relapse rates are staggering. Thus, novel, more targeted immunotherapies are needed that would be more effective, preferably without the need for a matched donor. Donor lymphocyte infusion (DLI), for the treatment of acute myeloid leukemia (AML) relapse after HSCT was introduced in 1990s. This approach consisted of the administration of lymphocytes from the original donor to the AML patient with relapsed disease. Yet, clinical benefits were limited and observed only in a minority of patients with smaller tumor burdens, and T cell mediated GVHD often further worsened the outcomes.

There is a great need for new and improved methodologies aimed at increasing NK cell numbers.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF SUMMARY

Disclosed are compositions comprising a plasma membrane vesicle, wherein the plasma membrane vesicle comprises an NK cell effector agent. NK cell effector agents can be a cytokine, an adhesion molecule, or an NK cell activating agent.

Disclosed are compositions comprising a plasma membrane vesicle, wherein the plasma membrane vesicle comprises an NK cell effector agent, wherein the NK cell effector agent can be IL-15, IL-21, IL-2, 41BBL, IL-12, IL-18, MICA, 2B4, LFA-1, or BCM1/SLAMF2.

Disclosed are compositions comprising a plasma membrane vesicle, wherein the plasma membrane vesicle comprises an NK cell effector agent, wherein the NK cell effector agent can be IL-15, IL-21, or 41BBL.

Disclosed are compositions comprising a plasma membrane vesicle, wherein the plasma membrane vesicle comprises an NK cell effector agent, wherein the plasma membrane can comprise two or more NK cell effector agents. At least one NK cell effector agent can be a cytokine. For example, disclosed are compositions comprising a plasma membrane vesicle, wherein the plasma membrane vesicle comprises an NK cell effector agent, wherein the plasma membrane can comprise IL-15 and 41BBL. In some aspects, the plasma membrane can further comprise IL-21. Disclosed are compositions comprising a plasma membrane vesicle, wherein the plasma membrane vesicle comprises an NK cell effector agent, wherein the plasma membrane can comprise IL-21 and 41BBL.

Disclosed are compositions comprising a plasma membrane vesicle, wherein the plasma membrane vesicle comprises an NK cell effector agent, wherein the plasma membrane vesicle surrounds a microparticle.

Disclosed are compositions comprising two or more plasma membrane vesicles, wherein the plasma membrane vesicles comprise an NK cell effector agent.

Disclosed are compositions comprising at least one composition comprising a plasma membrane vesicle comprising an NK cell effector agent and at least one composition comprising a membrane self-inserting peptide conjugated to an NK cell effector agent.

Disclosed are compositions comprising a membrane self-inserting peptide conjugated to an NK cell effector agent. NK cell effector agents can be a cytokine, an adhesion molecule, or an NK cell activating agent. Disclosed are compositions comprising a membrane self-inserting peptide conjugated to an NK cell effector agent, wherein the NK cell effector agent can be IL-15, IL-21, IL-2, 41BBL, IL-12, IL-18, MICA, 2B4, LFA-1, and BCM1/SLAMF2.

Disclosed are compositions comprising a membrane self-inserting peptide conjugated to an NK cell effector agent, wherein the NK cell effector agent is IL-15, IL-21, or 41BBL.

Disclosed are compositions comprising a membrane self-inserting peptide conjugated to an NK cell effector agent, wherein the membrane self-inserting peptide is a molecule that promotes insertion into a membrane and can be human Fc, GPI, transmembrane T cell receptor, or pHLIP.

Disclosed are compositions comprising two or more compositions comprising a membrane self-inserting peptide conjugated to an NK cell effector agent.

Disclosed are methods of treating cancer comprising administering to a subject an effective amount of a composition comprising a plasma membrane vesicle comprising at least one NK cell effector agent. At least one NK cell effector agent can be a cytokine, an adhesion molecule, or an NK cell activating agent. In some aspects, the NK cell effector agent can be IL-15, IL-21, or 41BBL.

Disclosed are methods of treating cancer comprising administering to a subject an effective amount of a composition comprising a plasma membrane vesicle comprising two or more NK cell effector agents. At least one NK cell effector agent can be a cytokine. Thus, disclosed are methods of treating cancer comprising administering to a subject an effective amount of a composition comprising a plasma membrane vesicle comprising two or more NK cell effector agents, wherein the plasma membrane can comprise IL-15 and 41BBL. In some aspects, the plasma membrane can further comprise IL-21. Also disclosed are methods of treating cancer comprising administering to a subject an effective amount of a composition comprising a plasma membrane vesicle comprising two or more NK cell effector agents, wherein the plasma membrane can comprise IL-21 and 41BBL. Also disclosed are methods of treating cancer comprising administering to a subject an effective amount of a composition comprising a plasma membrane vesicle comprising two or more NK cell effector agents, wherein the plasma membrane vesicle comprises IL-15 and IL-21.

Disclosed are methods of treating cancer comprising administering to a subject an effective amount of a composition comprising a plasma membrane vesicle comprising at least one NK cell effector agent, wherein the plasma membrane vesicle can be purified from NK cell feeder cells. NK cell feeder cells can be irradiated autologous or allogeneic peripheral blood mononuclear cells (PBMCs), RPMI8866, HFWT, K562, K562 cells transfected with membrane bound IL-15 and 41BBL), K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

Disclosed are methods of treating cancer comprising administering to a subject an effective amount of a composition comprising a plasma membrane vesicle comprising at least one NK cell effector agent, wherein an effective amount of the composition stimulates expansion of NK cells. Any of the disclosed plasma membrane vesicle compositions can be used in these methods.

Disclosed are methods of treating cancer comprising administering to a subject an effective amount of a composition comprising a membrane self-inserting peptide conjugated to an NK cell effector agent. An effective amount of the composition can stimulate expansion of NK cells.

Disclosed are methods of treating cancer comprising administering to a subject an effective amount of a composition comprising a membrane self-inserting peptide conjugated to an NK cell effector agent, wherein the composition comprises a membrane self-inserting peptide conjugated to IL-15, IL-21, or 41BBL.

Disclosed are methods of treating cancer comprising administering to a subject an effective amount of a composition comprising a membrane self-inserting peptide conjugated to an NK cell effector agent, wherein the membrane self-inserting peptide can be human Fc, GPI, transmembrane T cell receptor, or pHLIP.

Disclosed are methods of treating cancer comprising administering to a subject an effective amount of a composition comprising a membrane self-inserting peptide conjugated to an NK cell effector agent, wherein the composition can comprise two or more membrane self-inserting peptides conjugated to an NK cell effector agent.

Disclosed are methods of expanding NK cells comprising administering to a cell population an effective amount of a composition comprising a plasma membrane vesicle comprising at least one NK cell effector agent, wherein the cell population comprises NK cells. NK cell effector agents can be a cytokine, adhesion molecule or NK cell activating agent. In some aspects, the NK cell effector agent can be IL-15, IL-21 or 41BBL.

Disclosed are methods of expanding NK cells comprising administering to a cell population an effective amount of a composition comprising a plasma membrane vesicle comprising at least one NK cell effector agent, wherein the cell population comprises NK cells, wherein the plasma membrane vesicle comprises IL-15 and IL-21. In some aspects, the plasma membrane vesicle can further comprise 41BBL.

Disclosed are methods of expanding NK cells comprising administering to a cell population an effective amount of a composition comprising a plasma membrane vesicle comprising at least one NK cell effector agent, wherein the cell population comprises NK cells, wherein the plasma membrane vesicle comprises IL-15 and 41BBL. In some aspects, the plasma membrane vesicle can comprise IL-21 and 41BBL.

Disclosed are methods of expanding NK cells comprising administering to a cell population an effective amount of a composition comprising a plasma membrane vesicle comprising at least one NK cell effector agent, wherein the cell population comprises NK cells, wherein the plasma membrane vesicle can be purified from NK cell feeder cells. NK cell feeder cells can be irradiated autologous or allogeneic peripheral blood mononuclear cells (PBMCs), RPMI8866, HFWT, K562, K562 cells transfected with membrane bound IL-15 and 41BBL), K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

Disclosed are methods of expanding NK cells comprising administering to a cell population an effective amount of a composition comprising a plasma membrane vesicle comprising at least one NK cell effector agent, wherein the cell population comprises NK cells, wherein an effective amount of the composition stimulates expansion of NK cells.

Disclosed are methods of expanding NK cells comprising administering to a cell population an effective amount of a composition comprising a plasma membrane vesicle comprising at least one NK cell effector agent, wherein the cell population comprises NK cells, wherein administering to a cell population comprises administering the composition to a subject, wherein the subject comprises the cell population.

Disclosed are methods of expanding NK cells comprising administering to a cell population an effective amount of the composition comprising a membrane self-inserting peptide conjugated to an NK cell effector agent, wherein the cell population comprises NK cells. An effective amount of the composition can stimulate expansion of NK cells.

Disclosed are methods of expanding NK cells comprising administering to a cell population an effective amount of the composition comprising a membrane self-inserting peptide conjugated to an NK cell effector agent, wherein the cell population comprises NK cells, wherein the composition comprises a membrane self-inserting peptide conjugated to IL-15, IL-21, or 41BBL.

Disclosed are methods of expanding NK cells comprising administering to a cell population an effective amount of the composition comprising a membrane self-inserting peptide conjugated to an NK cell effector agent, wherein the cell population comprises NK cells, wherein the membrane self-inserting peptide can be human Fc, GPI, transmembrane T cell receptor, or pHLIP.

Disclosed are methods of expanding NK cells comprising administering to a cell population an effective amount of the composition comprising a membrane self-inserting peptide conjugated to an NK cell effector agent, wherein the cell population comprises NK cells, wherein administering to a cell population comprises administering the composition to a subject, wherein the subject comprises the cell population.

Disclosed are methods of expanding NK cells comprising administering to a cell population an effective amount of the composition comprising a membrane self-inserting peptide conjugated to an NK cell effector agent, wherein the cell population comprises NK cells, wherein the composition comprises at least two membrane self-inserting peptide conjugates, wherein the membrane self-inserting peptide conjugates are conjugated to an NK cell effector agent. At least two membrane self-inserting peptide conjugates can be conjugated to the same or different NK cell effector agents.

Disclosed are methods of modulating the immune system comprising administering to a subject one or more of the compositions comprising a membrane self-inserting peptide conjugated to an NK cell effector agent or a plasma membrane vesicle comprising an NK cell effector agent. Methods of modulating the immune system can comprise reducing the number of activated T cells, expanding the number of NK cells, or reducing the number of dendritic cells.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 8A and 8B depict debris found in cultures after NK cell expansion. a) FSC vs. SSC of PBMC (red) together with plasma membrane at day 10 of culture. b) FSC vs. SSC of PBMC (red) together with K562mb15 feeder cell debris (green). The top and bottom figures represent separate cultures on day 10. The top figure has significantly more feeder cell debris vs. the bottom figure.

DETAILED DESCRIPTION

Figure 1:
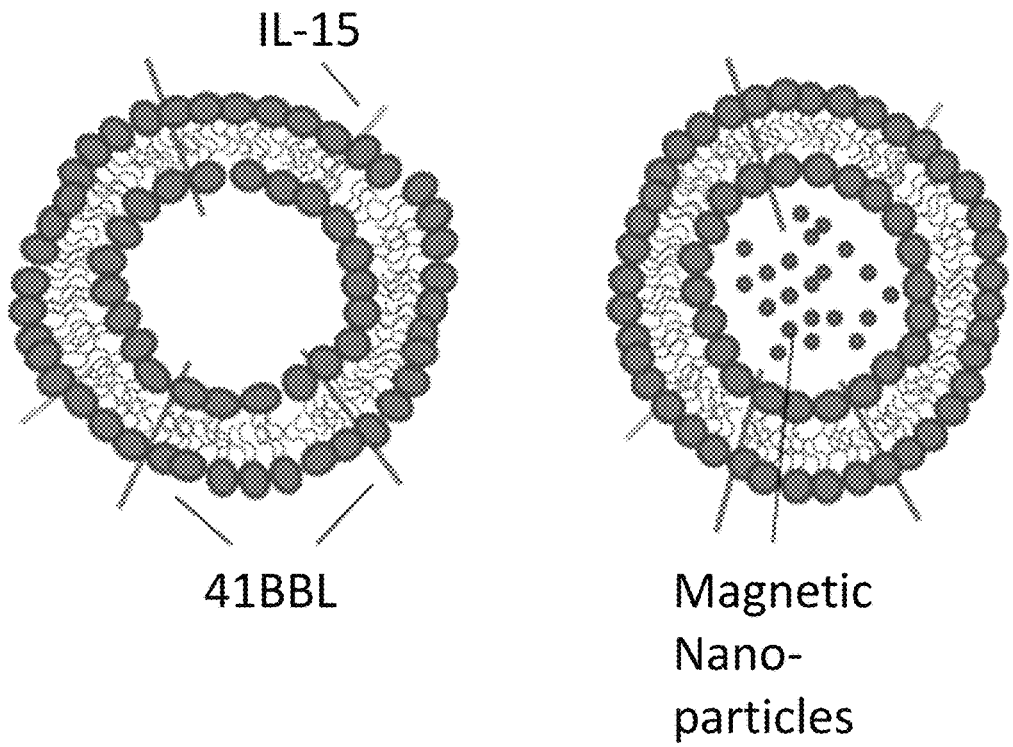
FIG. 1 is a depiction of a plasma membrane from K562-mb15-41BBL cells containing stimulatory ligands (IL-15 and 41BBL) either alone or loaded with magnetic nanoparticles, a C18 silica or polystyrene bead, or a silica bead.
Figure 1:
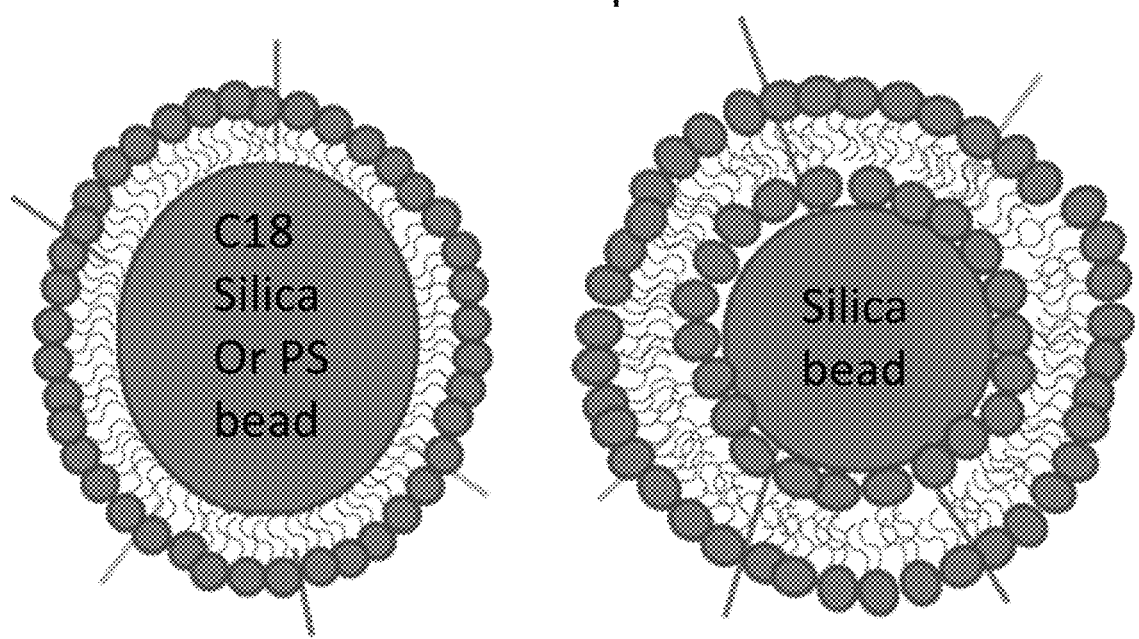
Figure 2:
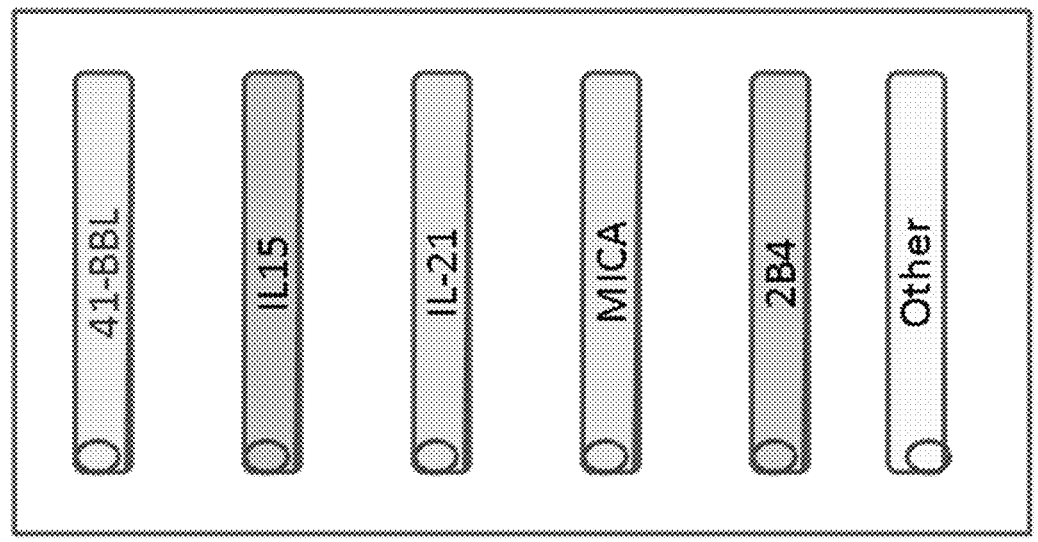
FIG. 2 is a representation of NK cell effector agents, which include 41-BBL, IL-15, IL-21, MICA, 2B4, and other. The other includes but is not limited to BCM1/SLAMF2, IL-2, IL-12. Also shown is a generic membrane self-inserting peptide (MBI). The NK cell effect agent and MBI can be crosslinked together and self-insert into tumor cells.
Figure 2:
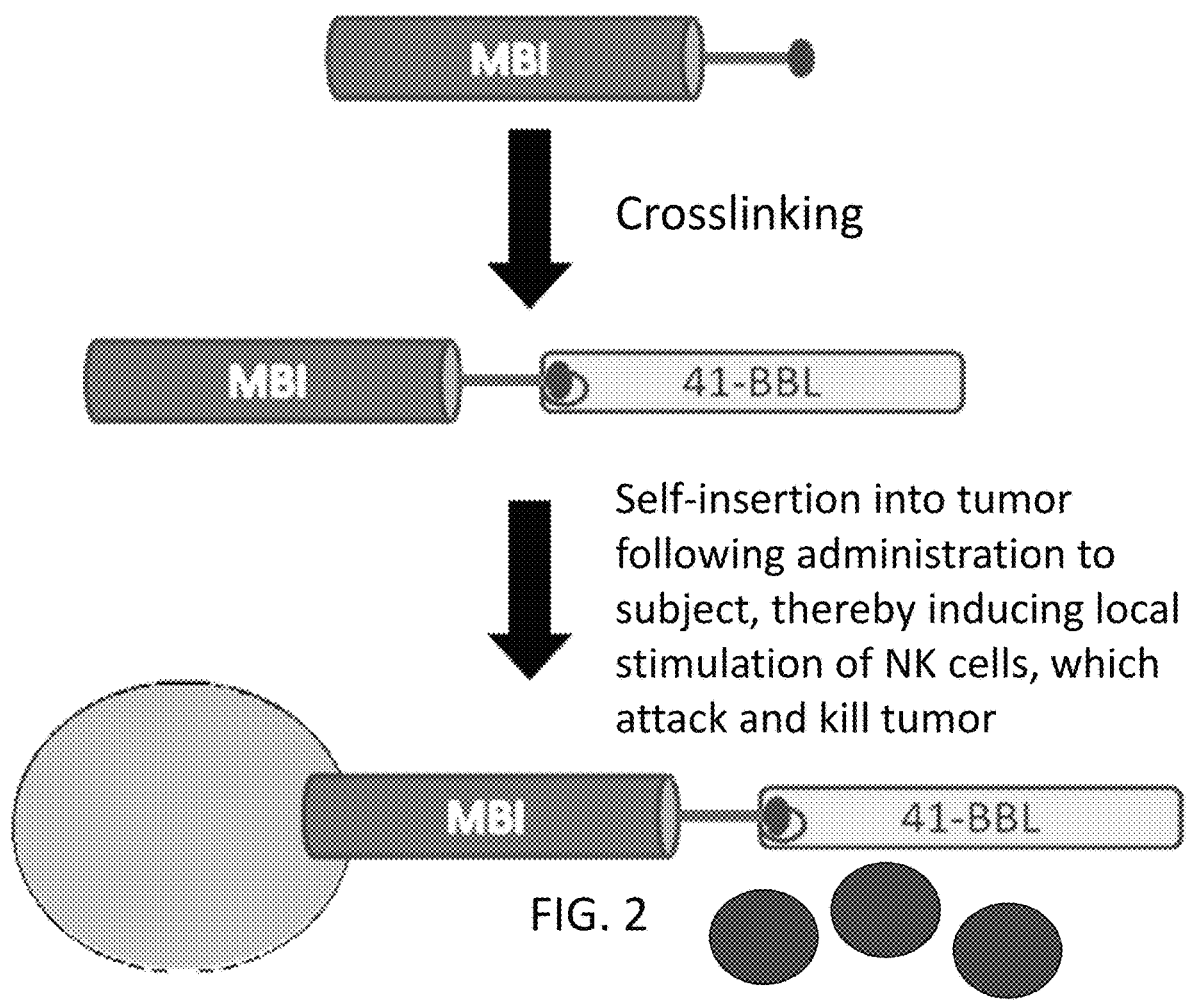

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A significant portion of donor lymphocyte infusion mediated graft-versus-tumor (GVT) effect may be due to natural killer (NK) cells. The infusion of NK cells isolated from donor blood could produce beneficial GVT effects without causing GVHD. Preclinical and clinical data has shown effectiveness of NK cell infusions leading toward complete remission without any GVHD. Thus, NK cell infusion, in combination with autologous transplantation, or as a stand-alone treatment, offers an innovative, and potentially very effective, alternative for those patients who do not have a matched donor, experience relapse, or do not qualify for transplant.

Infusions of NK cells are a treatment option for patients with cancers susceptible to NK cell lysis, including blood cancers (such as acute myeloid leukemia or multiple myeloma) and several solid tumors (e.g. brain tumor, Ewing sarcoma and rhabdomyosarcoma) (Harada, Saijo et al. 2002; Ruggeri, Capanni et al. 2002; Miller, Soignier et al. 2005; Cho, Shook et al. 2010). Increased numbers of functional NK cells can also significantly enhance the efficacy of therapeutic antibodies used in treatment of several cancers, including lymphomas, colorectal cancer, lung cancer, and breast cancer, among others (Hatjiharissi, Xu et al. 2007; Triulzi, Vertuani et al. 2010; Houot, Kohrt et al. 2011; Tai, Horton et al. 2012). These types of personalized treatments are, however, very costly, with a typical antibody-containing regimen costing tens of thousands of dollars. Furthermore, the expected efficacy of existing methods is often not achieved due to the lack of immune cell engagement in immune compromised cancer patients (Dewan, Takada et al. 2009; Mamessier, Sylvain et al. 2011).

To be effective as a cancer treatment method, it is desirable to achieve a degree of NK cell expansion that reaches an effective therapeutic dose. Several studies have shown that NK cells proliferate in an in vitro culture exponentially and preferentially within a mixture of peripheral blood mononuclear cells (PBMC) when stimulated with a combination of cytokines (such as IL-15 or IL-21) and ligands for activating receptors (such as 4-1BBL) expressed on the surface of stimulator cells (Imai, Iwamoto et al. 2005; Cho and Campana 2009; Lee, Verneris et al. 2010; Somanchi, Senyukov et al. 2011).

For cytokines IL-15 and IL-21, cross-presentation of membrane bound interleukin, as in normal dendritic cells, induces expansion of NK cells more potently than the soluble form of these cytokines. Moreover, under such stimulation conditions, only a low concentration of soluble IL-2 is required for NK cell survival, thus allowing for selective expansion of NK cells within a PBMC mixture without observable proliferation of T cells. The soluble form of IL-15 and IL-21 cytokines or high dose IL-2 stimulate more potently the proliferation of T cells than of NK cells. A previously published study by Campana and coworkers has shown that in an in vitro culture stimulation of NK cells with the K562 cell line having membrane bound IL-15 and 4-1BBL leads to a potent expansion of NK cells that is not observed with K562 cells expressing either of the molecules alone (Imai, Iwamoto et al. 2005; Fujisaki, Kakuda et al. 2009). However, NK cell expansion was limited to several divisions and the cells achieved senescence and stopped proliferating, coinciding with the observation of telomere shortening. In a follow-up study, stimulation with membrane bound IL-21 instead of IL-15 was found to stimulate continuous propagation of NK cells over countless generations allowing for continuous expansion of NK cells provided that the culture is periodically replenished with fresh stimulatory cells (Somanchi, Senyukov et al. 2011; Denman, Senyukov et al. 2012). While these methods allow for efficient in vitro NK cell expansion, the need for live feeder cells makes the methodology difficult to transfer to clinical settings. Also, NK cells that are infused into the patient will likely stop dividing due to the lack of continued stimulation by the feeders. Furthermore, there is still a lack of information about the ability of in vitro cultured NK cells to function as intended when re-infused into a patient (Miller 2009).

Currently IL-2 administration is the only FDA approved method of expansion of NK cells in vivo. IL-15 is currently being tested in a Phase I clinical trial as an alternative approach to IL-2 administration but based on preclinical findings it is still expected to have significant toxicity if administered systematically. Thus, both methods carry significant toxicities to patients and also induce proliferation of T-cells including regulatory T-cells leading to short persistence (on average less than 21 days) of NK cells.

A successful pilot trial showed that infusion of purified NK cells isolated from donor's blood is safe and can lead to complete remission of AML, with no GVHD. To reach the therapeutic dose, NK cells were expanded in vivo in lymphodepleted patients by daily administration of high dose IL-2. However, the intensive conditioning regimen required for lymphodepletion and the high doses of IL-2 used in this study resulted in significant toxicity and prolonged hospitalization, and in many cases, low in vivo expansion on NK cells. Moreover, systemic administration of IL-2 leads to proliferation of regulatory T cells that suppress the numbers and function of NK cells, thereby limiting their persistence and efficiency in the patient. Thus, alternative approaches for in vivo or ex vivo expansion of NK cells are needed.

The efficacy of NK cell immunotherapy is dependent on the dose of NK cells administered to the patient or reached after infusion through in vivo expansion. Currently available techniques are limited by their inability to achieve the level of NK cell expansion required to achieve a therapeutic effect in a patient. The lack of a clinical expansion protocol is a major barrier to the progress of NK cell-based immunotherapy. Current ex vivo expansion protocols use a combination of high dose cytokines with activating ligands expressed on leukemia-derived feeder/stimulator cell lines, posing a significant downside for transfer to clinical settings in most centers and are not amenable for direct in vivo expansion. The use of particle technology described herein eliminates the need for stimulator cells, thus simplifying the methodology and allowing direct and selective in vivo expansion.

Several groups have pursued a method to expand NK cells ex vivo. However, most of the currently developed ex vivo methods rely on co-culture systems of tumor cell lines and NK cells in the presence of high concentrations of various cytokines, mostly IL-2 (Reviewed in Cho and Campana 2009; Suck and Koh 2010). Cells used to trigger NK cell proliferation include irradiated autologous or allogeneic PBMCs, RPMI8866, HFWT, K562, K562-mb15-41BBL (K562 transfected with 4-1BBL and membrane-bound IL-15), K562-mb21-41BBL and EBV-LCL(Harada, Saijo et al. 2004; Imai, Iwamoto et al. 2005; Berg, Lundqvist et al. 2009; Fujisaki, Kakuda et al. 2009; Siegler, Meyer-Monard et al. 2010). Although expansion of NK cells can be significant with some of these cell lines (30-10,000 fold within 7-21 days), the use of feeder cells poses significant downsides for transfer into a clinical setting in most centers due to the requirement for a current Good Manufacturing Practice (cGMP) facility, which costs several million dollars (Reviewed in Cho and Campana 2009; Suck and Koh 2010). Furthermore, continuous culturing of feeder cells is costly and requires support of dedicated personnel. The National Institutes of Health (NIH) currently provides support in the manufacturing of cells for cellular therapy in the form of Production Assistance for Cellular Therapy (PACT). However, NK cells appear to lose their activity during cryopreservation (PACT workshop presentation). Thus, the storage and transport of expanded NK cells from the site of production to the transplant center is another obstacle in successful application of the therapy. An additional concern is the potential for infusion of live feeder cells and/or genetic material released from those transformed cells and culture components (e.g. fetal bovine serum) into a recipient patient.

Miltenyi Biotech has introduced an in vitro expansion kit that uses antibody-coated beads to crosslink activating NK cell receptors. However, this method requires the use of high concentration IL-2. While useful for laboratory applications, this method cannot be transferred to clinical settings because NK cells cultured using high concentrations of cytokines undergo rapid apoptosis after infusion due to cytokine withdrawal (Miller 2009).

Expansion of NK cells within PBMC has been reported with a high concentration of IL-2 and stimulation with anti-CD3 antibody for the first five days (Carlens, Gilljam et al. 2001; Alici, Sutlu et al. 2008). The overall NK cell expansion was close to 1000-fold, but most of the NK cells were actually NK-like T cells (Berg and Childs 2010). Thus, all of the methods pose significant difficulties for the transfer to clinical applications and none of the methods can be used in direct in vivo expansion.

A. Plasma Membrane Vesicles

Disclosed are plasma membrane vesicles comprising at least one NK cell effector agent. NK cell effector agents can be a cytokine, an adhesion molecule, or an NK cell activating agent (i.e. stimulatory ligand). Examples of cytokines can be, but are not limited to, IL-2, IL-12, IL-15, IL-21, and IL-18. Examples of adhesion molecules can be, but are not limited to LFA-1, MICA, BCM/SLAMF2. Examples of NK cell activating agents can be, but are not limited to, 41BBL and BCM/SLAMF2. In some aspects, a member of one group can also be a member of another group. For example, BCM/SLAMF2 can be both an adhesion molecule and NK cell activating agent. The NK cell effector agent can be but is not limited to, 41BBL, IL-2, IL-12, IL-15, IL-21, IL-18, MICA, LFA-1, 2B4, and BCM/SLAMF2. Plasma membrane vesicles are vehicles used to carry NK cell effector agents. The NK cell effector agents can be membrane bound. While the NK cell effector agents are membrane bound, other therapeutic or diagnostic agents can be transported in the interior of the plasma membrane vesicle.

In some aspects, the plasma membrane vesicle comprises at least one membrane bound cytokine. Thus, disclosed are plasma membrane vesicles, wherein the plasma membrane vesicle comprises an NK cell effector agent, wherein the NK cell effector agent is IL-15, IL-21 or 41BBL.

Disclosed are compositions comprising a plasma membrane vesicles, wherein the plasma membrane vesicle comprises two or more NK cell effector agents. In some aspects, at least one NK cell effector agent can be a cytokine. For example, the plasma membrane can comprise IL-15 and 41BBL; IL-15, 41BBL and IL-21; or IL-21 and 41BBL. In some aspects, the plasma membrane vesicle comprises at least two membrane bound cytokines. For example, a plasma membrane vesicle can comprise membrane bound IL-15 and membrane bound IL-21.

The plasma membrane vesicles can be used alone, loaded with magnetic nanoparticles or mounted on a solid surface such as but not limited to a silica or latex bead. In some aspects, plasma membrane vesicles can surround or coat a microparticle. Plasma membrane coated microparticles can be made with any of the plasma membrane vesicles described herein. For example, disclosed are microparticles coated with a plasma membrane comprising IL-15 and 41BBL or IL-21 and 41BBL. The plasma membrane coated microparticles can be loaded with magnetic particles, silica beads, polystyrene beads, latex beads, contrasting agents, or known therapeutics, such as cancer therapeutics.

Disclosed are compositions comprising two or more plasma membrane vesicles, wherein the plasma membrane vesicles comprise an NK cell effector agent. For example, compositions can comprise a plasma membrane vesicle that contains IL-15 and 41BBL and a plasma membrane vesicle that contains IL-21 and 41BBL.

Disclosed are compositions comprising at least one composition comprising a membrane self-inserting peptide conjugated to an NK cell effector agent and at least one composition comprising a plasma membrane vesicle, wherein the plasma membrane vesicle comprise an NK cell effector agent. The NK cell effector agent conjugated to the membrane self-inserting peptide can be the same or different from the NK cell effector agent present in the plasma membrane vesicle.

Plasma membrane vesicles are vesicles made from the plasma membrane of a cell or artificially made (i.e. liposomes). Plasma membrane vesicles can be prepared using any of the techniques known in the art. For example, common plasma membrane preparation protocols can be used or common protocols for preparing liposomes. The plasma membrane vesicle can contain a lipid bilayer or simply a single layer of lipids. Artificially made plasma membranes, such as liposomes, can be prepared using a lipid bilayer and membrane self-inserting peptide conjugates as described below.

B. Membrane Self-Inserting Peptides Conjugates

Disclosed are compositions comprising a membrane self-inserting peptide conjugated to an NK cell effector agent. These compositions can also be referred to as membrane self-inserting peptide conjugates.

NK cell effector agents can be a cytokine, an adhesion molecule, or an NK cell activating agent (i.e. stimulatory ligand). Examples of cytokines can be, but are not limited to, IL-2, IL-12, IL-15, IL-21, and IL-18. Examples of adhesion molecules can be, but are not limited to LFA-1, MICA, BCM/SLAMF2. Examples of NK cell activating agents can be, but are not limited to, 41BBL and BCM/SLAMF2. In some aspects, a member of one group can also be a member of another group. For example, BCM/SLAMF2 can be both an adhesion molecule and NK cell activating agent. The NK cell effector agent can be but is not limited to, 41BBL, IL-2, IL-12, IL-15, IL-21, IL-18, MICA, LFA-1, 2B4, and BCM/SLAMF2. Thus, disclosed are compositions comprising a membrane self-inserting peptide conjugated to an NK cell effector agent, wherein the NK cell effector agent can be IL-15, IL-21 or 41BBL.

Disclosed are compositions comprising a membrane self-inserting peptide conjugated to an NK cell effector agent, wherein the membrane self-inserting peptide is a molecule that promotes insertion into a membrane and can be human Fc, GPI, transmembrane T cell receptor, or pHLIP. The membrane self-inserting peptide can be any peptide known to insert into a cell membrane. Depending on the use of the membrane self-inserting peptide conjugate, certain membrane self-inserting peptides can be better choices than others. One of skill in the art would understand what membrane self-inserting peptide is ideal under different circumstances. For example, for in vivo use, pHLIP membrane self-inserting peptide can be used. pHLIP membrane self-inserting peptides insert into the membrane only under conditions of low pH. Therefore, pHLIP conjugates will not insert into cell membranes under normal physiological conditions. However, upon injection into a tumor environment, the pHLIP conjugate can insert into the cell membrane of tumor cells because the tumor environment is more acidic than normal physiological conditions. This insertion into the tumor environment allows for activation of NK cells in the area of the tumor. Using pHLIP thus prevents unwanted insertion into random cell membranes.

Disclosed are compositions comprising two or more membrane self-inserting peptide conjugates, wherein the membrane self-inserting conjugates are conjugated to an NK cell effector agent. Any of the disclosed membrane self-inserting conjugates described herein can be used in these compositions. The two or more membrane self-inserting conjugates can have the same or different NK cell effector agent.

The membrane self-inserting peptides can be conjugated to an NK cell effector agent in a variety of ways. Techniques for conjugating are well known in the art. In some aspects, the membrane self-inserting peptide conjugates can be fusion proteins. Fusion-proteins can be produced in bacterial cells. The fusion proteins can consist of the NK cell effector agent conjugated to a lipophilic molecule such as hydrophobic peptide, GPI, or human Fc for anchoring into liposomes or cellular membranes (Hunt, Rath et al. 1997; Kueng, Leb et al. 2007; Paulick, Forstner et al. 2007; Paulick, Wise et al. 2007; Reshetnyak, Segala et al. 2007). cDNA vectors for these fusion proteins can be ligated into an expression plasmid, which allows expression in bacterial (*E. coli*), insect, or mammalian cells. The cDNA vector can be FLAG- or HIS-tagged. Bacterial cells can be transfected using standard CaCl transfection methods, such as that described in Sambrook et al., Molecular Cloning: A Laboratory Manual. 2nd ed. Cold Spring Harbor Laboratory Press (1989). Bacterial cells can be cultured in LB media and cells can be harvested and lysed using a French Press. Proteins of interest can be purified from lysates by affinity chromatography. Palmitate-conjugated protein A and purified Fc fusion proteins can be conjugated as described in the literature by mixing 1:2 (w/w) at 4 degrees C. (see Kim & Peacock, Journal of Immunological Methods, 1993 Jan. 14; 158(1): 57-65 and Liu et al., Journal of Immunology, 2007 Mar. 1; 178(5); 3301-3306). The conjugates can then be directly injected intratumorally or can be incorporated into liposomes.

Membrane self-inserting peptide conjugates can be incorporated into liposomes. For example, GPI can be coupled with 41BBL, IL-2, IL-12, IL-15, IL-21, MICA, 2B4, or BCM/SLAMF1 and can be incorporated into liposomes.

Liposomes can be prepared by dissolving lipids in chloroform and evaporating under nitrogen to form a film. Small unilamellar liposomes can be formed by resuspending lipids in water and sonicating with a bath sonicator. Either protein A/Fc fusion protein conjugates or GPI coupled proteins can be mixed with liposomes. Protein insertion can be such that the protein A or GPI anchor can insert into the lipid bilayer, leaving the functional stimulatory protein on the extracellular region. Liposomes can then be PEGylated to increase lifetime. Protein-coated liposomes can then be used for cancer therapy by ex vivo expansion of immune effector cells or by direct intravenous injection to promote in vivo expansion/activation of immune cells.

Types of conjugation and methods for conjugating are known to the art. The term "conjugate" refers to the membrane self-inserting peptide being conjugated, coupled, or linked to another composition such as a peptide or protein. For example, membrane self-inserting peptide conjugates can be fusion proteins wherein the membrane self-inserting peptide is conjugated to another protein via a disulfide bond. Coupling or conjugating can mean that there is a chemical linkage between the membrane self-inserting peptide and the NK cell effector agent.

In some aspects, the NK cell effector agent can be conjugated to membrane self-inserting peptides or GPI anchors for in situ self-assembly. For example, 41-BBL and IL-21 can be conjugated into a pHLIP peptide which inserts itself into cellular membranes under acidic conditions, thereby allowing the anchoring of the stimulatory ligands into cells in the proximity of tumor (Reshetnyak, et al. 2006; Andreev, et al. 2007; Reshetnyak, et al. 2007). The NK cell effector agents 41BBL, IL-2, 11-12, IL-15, IL-21, and BCM/SLAMF2 can be produced in bacterial cells or purchased from commercially available sources. cDNA vectors for these proteins can be ligated into pTriEX expression plasmid which allows expression in bacterial (*E. coli*), insect, or mammalian cells. The cDNA vector can code for expression of FLAG- or HIS-tag. Bacterial cells can be transfected using standard CaCl transfection methods. Bacterial cells can be cultured on LB media. Cells can be harvested and lysed using a French press. Proteins of interest can then be purified from lysates by affinity chromatography.

pHLIP can be prepared by solid-phase peptide synthesis using 9-fluorenylmethyloxycarbonyl chemistry and the product can be purified on a C18 column by reverse-phase chromatography. pHLIP can then be conjugated to stimulatory human protein ligands by incubating with a crosslinker, such as benzophenone-4-iodoacetamide. After several washes, the conjugated pHLIP protein can be resuspended in media (saline, for example) and injected intratumorally or intravenously. Based on evidence from prior literature (Imai, Iwamoto et al. 2005; Liu, Breiter et al. 2007; Fujisaki, Kakuda et al. 2009; Somanchi, Senyukov et al. 2011; Denman, Senyukov et al. 2012) and presented experimental results, interaction of NK cells with stimulatory ligands such as IL-21 or IL-15 and 41-BBL on the surface of such modified tumor cells can stimulate in situ NK cell expansion and trigger their cytotoxic response toward a tumor. This type of stimulatory approach can be used for treatments of solid tumors such as ovarian cancer where NK stimulatory ligands that insert in situ into tumor cells under acidic pH can be injected into intraperitoneal space of patients with low dose IL-2 alone or together with NK cells (Geller, Cooley et al. 2011). There is strong evidence that cytotoxic lymphocytes that express high levels of FCγIII R (CD16) such as NK cells are crucial for the efficacy of cancer therapy with therapeutic antibodies(Kute, Savage et al. 2009; Reim, Dombrowski et al. 2009; Mamessier, Sylvain et al. 2011). Thus, this approach can also be used in combination with therapeutic antibodies.

C. Combination of Plasma Membrane Vesicles and Membrane Self-Inserting Peptide Conjugates Disclosed are compositions comprising one or more of the disclosed plasma membrane vesicles and one or more of the disclosed membrane self-inserting peptide conjugates. The plasma membrane vesicle and the membrane self-inserting peptide conjugate can comprise the same NK cell effector agent or different NK cell effector agents.

D. Methods of Expanding Natural Killer Cells

Disclosed are methods of expanding NK cells comprising administering to a cell population an effective amount of a composition comprising a plasma membrane vesicle comprising at least one NK cell effector agent, wherein the cell population comprises NK cells.

Disclosed are methods of expanding NK cells comprising administering to a cell population an effective amount of a composition comprising a membrane self-inserting peptide conjugated to an NK cell effector agent, wherein the cell population comprises NK cells.

Also disclosed are methods of expanding NK cells comprising administering a composition that comprises one of the disclosed plasma membrane vesicles and a composition comprising one of the disclosed membrane self-inserting peptide conjugates. In some aspects, one composition can be formulated to contain one or more plasma membrane vesicles and one or more membrane self-inserting peptide conjugates.

Expanded NK cells and/or compositions used to expand NK cells can be used as a treatment method for patients having cancers that are susceptible to NK cell mediated lysis as well as for patients who have undergone hematopoietic stem cell transplant. NK cell expanding compositions can be used to increase the amount of cytotoxic NK cells after stem cell transplant for increased clearance of residual tumor cells and/or for relapse prevention. The NK cell-expanding compositions can also be used to treat patients with viral infection.

NK cell expanding compositions can be used as a post NK cell infusion treatment method to increase the numbers and in vivo persistence of cytotoxic NK cells for increased efficacy of NK cell therapy (i.e. number of patients that achieve remission and/or remain in remission).

NK cells with or without NK cell-expanding compositions will be used in combination with therapeutic antibodies for treatment of various cancers including, but not limited to, lymphomas, colorectal, lung, colon, head and neck, and breast cancers to increase the number of patients that respond to the therapeutic antibody therapy and achieve remission and/or remain in remission.

1. Expanding NK Cells with Plasma Membrane Vesicles

Plasma membrane vesicles comprising at least one NK cell effector agent can be used to expand NK cells in vitro or in vivo. The methods of expanding NK cells can comprise administering to a cell population an effective amount of a composition comprising a plasma membrane vesicle comprising at least one NK cell effector agent.

NK cell effector agents can be a cytokine, adhesion molecule or NK cell activating agent. Disclosed are methods of expanding NK cells comprising administering to a cell population an effective amount of a composition comprising a plasma membrane vesicle comprising at least one NK cell effector agent, wherein the cell population comprises NK cells, wherein the NK cell effector agent can be IL-15, IL-21 or 41BBL. In some aspects, the plasma membrane vesicle can comprise any combination of NK cell effector agents. For example, a plasma membrane vesicle can comprise IL-15 and IL-21; IL-15 and 41BBL; IL-21 and 41BBL; or IL-15, IL-21 and 41BBL. Thus, a plasma membrane vesicle containing any combination of one or more of IL-15, IL-21 and 41BBL can be used to expand NK cells.

Disclosed are methods of expanding NK cells comprising administering to a cell population an effective amount of a composition comprising a plasma membrane vesicle comprising at least one NK cell effector agent, wherein the plasma membrane vesicle can be purified from NK cell feeder cells. The NK cell feeder cells can be irradiated autologous or allogeneic peripheral blood mononuclear cells (PBMCs), RPMI8866, HFWT, K562, K562 cells transfected with membrane bound IL-15 and 41BBL), K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

In some aspects, the plasma membrane vesicles used in the methods to expand NK cells can be derived from any cell type. The plasma membrane of any cell can be altered to contain the NK cell effector agents of interest.

Disclosed are methods of expanding NK cells comprising administering to a cell population an effective amount of a composition comprising a plasma membrane vesicle comprising at least one NK cell effector agent, wherein an effective amount of the composition comprising a plasma membrane vesicle comprising at least one NK cell effector agent stimulates expansion of NK cells.

Disclosed are methods of expanding NK cells comprising administering to a cell population an effective amount of a composition comprising a plasma membrane vesicle comprising at least one NK cell effector agent, wherein administering to a cell population comprises administering the composition to a subject, wherein the subject comprises the cell population.

In some aspects of the methods, cytotoxic NK cells selectively expand in vivo in the presence of a combination of NK cell effector agents including but not limited to membrane bound cytokines, adhesion molecules and NK cell activating agents. The NK cell effector agents can be delivered in a form of an empty or loaded cell membrane vesicle, liposome, cell membrane coated bead or lipid coated bead (FIG. 1). The molecules that can be loaded into the plasma membrane vesicles include, but are not limited to, IL-2 for local delivery to the site of NK-cell expansion, contrasting agents for detection to monitor bio-distribution and clearance, or super-magnetic particles to deliver the particles to specific locations e.g. lymph nodes or tumors. The magnetic particles can also allow quick removal and detection.

2. Expanding NK Cells with Membrane Self-Inserting Peptide Conjugates

Disclosed are methods of expanding NK cells comprising administering to a cell population an effective amount of a composition comprising at least one membrane self-inserting peptides conjugated to an NK cell effector agent, wherein the cell population comprises NK cells. Membrane self-inserting peptides conjugated to an NK cell effector agent can be used to expand NK cells. Membrane self-inserting peptide conjugates can be administered as a peptide conjugate or they can be used to make a composition such as liposomes containing the membrane self-inserting peptide conjugates and then the liposomes can be administered.

Disclosed are methods of expanding NK cells comprising administering to a subject an effective amount of a composition comprising a membrane self-inserting peptide conjugated to an NK cell effector agent, wherein an effective amount of the composition comprising a membrane self-inserting peptide conjugated to an NK cell effector agent stimulates expansion of NK cells.

Disclosed are methods of expanding NK cells comprising administering to a cell population an effective amount of a composition comprising a membrane self-inserting peptide conjugated to an NK cell effector agent, wherein an effective amount of the composition stimulates expansion of NK cells.

Disclosed are methods of expanding NK cells comprising administering to a cell population an effective amount of a composition comprising a membrane self-inserting peptide conjugated to an NK cell effector agent, wherein the composition can comprise a membrane self-inserting peptide conjugated to IL-15. In some aspects, the composition can comprise a membrane self-inserting peptide conjugated to IL-21. In some aspects, the composition can comprise a membrane self-inserting peptide conjugated to 41BBL. In some aspects the NK cell effector agent is any cytokine, adhesion molecule or NK cell activating agent.

Disclosed are methods of expanding NK cells comprising administering to a cell population an effective amount of a composition comprising a membrane self-inserting peptide conjugated to an NK cell effector agent, wherein the membrane self-inserting peptide can be human Fc, GPI, transmembrane T cell receptor, or pHLIP.

Disclosed are methods of expanding NK cells comprising administering to a cell population an effective amount of a composition comprising a membrane self-inserting peptide conjugated to an NK cell effector agent wherein administering to a cell population comprises administering the composition to a subject, wherein the subject comprises the cell population.

Disclosed are methods of expanding NK cells comprising administering to a cell population an effective amount of a composition comprising a membrane self-inserting peptide conjugated to an NK cell effector agent, wherein the composition comprises at least two membrane self-inserting peptide conjugates, wherein the membrane self-inserting peptide conjugates are conjugated to an NK cell effector agent. The at least two membrane self-inserting peptide conjugates can be conjugated to the same or different NK cell effector agents. For example, the methods of expanding NK cells can include administering a composition that comprises a membrane self-inserting peptide conjugated to a cytokine and a membrane-self-inserting peptide conjugated to an NK cell activating agent. In some aspects, methods of expanding NK cells can comprise administering two or more separate compositions wherein each composition only contains one membrane self-inserting peptide conjugate.

3. NK Cells

Human NK cells are a subset of peripheral blood lymphocytes defined by the expression of CD56 or CD16 and the absence of T cell receptor (CD3) (Ljunggren and Malmberg 2007; Woan and Reddy 2007). NK cells sense and kill target cells that lack major histocompatibility complex (MHC)-class I molecules. NK cell activating receptors include, among others, the natural cytotoxicity receptors (NKp30, NKp44 and NKp46), and lectin-like receptors NKG2D and DNAM-1. Their ligands are expressed on stressed, transformed, or infected cells but not on normal cells, making normal cells resistant to NK cell killing (Bottino, Castriconi et al. 2005; Gasser, Orsulic et al. 2005; Lanier 2005). NK cell activation is negatively regulated via inhibitory receptors, such as killer immunoglobin (Ig)-like receptors (KIRs), NKG2A/CD94, and leukocyte Ig-like receptor-1 (LIR-1). Engagement of one inhibitory receptor may be sufficient to prevent target lysis (Bryceson, Ljunggren et al. 2009). Hence NK cells efficiently target cells that express many stress-induced ligands, and few MHC class I ligands.

NK cells efficiently destroy tumor cells, stressed cells, and virally infected cells by a variety of different methods. The first is by directly engaging target cells, permeating their membranes, and then injecting a protein that cleaves and activates several apoptotic proteins, thereby initiating programmed cell death (apoptosis) of the targeted cell. The surface of an NK cell also contains protein ligands that can bind and activate receptors, such as the receptor for tumor-necrosis factor (TNF)-related apoptosis-inducing ligand (TRAIL), on target cells that turn on internal signals for apoptotic programmed cell death. When stimulated, NK cells can also secrete cytokines such as INFγ and TNFα that not only inhibit viruses and tumors, but also signal invasion to other immune cells. This broad and multimodal anti-cancer activity of NK cells make them of great interest to the medical field.

Because NK cells have a prominent role in the immune system, the ability to expand NK cells provides treatment opportunities that were not possible or less effective with low numbers of NK cells.

4. Expanding NK Cells Provides Other Options for the NK Cells

The methods of expanding NK cells are beneficial for treating cancer, treating viral infections, studying NK cells, treating multiple sclerosis, immune surveillance, and treating graft versus host disease. Any NK cell related disorder can be treated or affected by the expansion of NK cells. For example, diseases such as multiple sclerosis that are known for having an increase in activated T cells can be treated with the disclosed compositions because these compositions cause an expansion of NK cells that target and kill activated T cells. Thus, the disclosed compositions can be used to decrease activated T cells.

E. Methods of Treating Cancer

Disclosed are methods of treating cancer comprising administering to a subject an effective amount of a composition comprising a plasma membrane vesicle comprising at least one NK cell effector agent.

Disclosed are methods of treating cancer comprising administering to a subject an effective amount of a composition comprising a membrane self-inserting peptide conjugated to an NK cell effector agent.

Treating cancer with a plasma membrane vesicle comprising at least one NK cell effector agent or a membrane self-inserting peptide conjugated to an NK cell effector agent can occur due to the expansion of NK cells in the presence of these compositions. The expansion of NK cells leads to more NK cells able to target and kill tumor cells, thus reducing tumor cells and ultimately treating cancer.

The plasma membrane vesicle comprising at least one NK cell effector agent or membrane self-inserting peptide conjugated to an NK cell effector agent can provide a preventative effect. NK cells are known to provide immunosurveillance. Therefore, administering a composition that results in expansion of NK cells allows for more NK cells to provide immunosurveillance and to target and kill pre-cancerous cells before cancer occurs.

In some aspects, administering to a subject can include administering the disclosed compositions to a cell population in vitro and then administering those treated cells to a subject.

1. Treating with Plasma Membrane Vesicles

Plasma membrane vesicles comprising at least one NK cell effector agent can be used to treat cancer. The methods of treating cancer can comprise administering to a subject an effective amount of a composition comprising a plasma membrane vesicle comprising at least one NK cell effector agent.

NK cell effector agents can be a cytokine, adhesion molecule or NK cell activating agent. Disclosed are methods of treating cancer comprising administering to a subject an effective amount of a composition comprising a plasma membrane vesicle comprising at least one NK cell effector agent, wherein the NK cell effector agent can be IL-15, IL-21 or 41BBL. In some aspects, the plasma membrane vesicle can comprise any combination of NK cell effector agents. The plasma membrane can comprise two or more NK cell effector agents. In some aspects, at least one NK cell effector agent can be a cytokine. For example, a plasma membrane vesicle can comprise IL-15 and IL-21; IL-15 and 41BBL; IL-21 and 41BBL; or IL-15, IL-21 and 41BBL. Thus, a plasma membrane vesicle containing any combination of one or more of IL-15, IL-21 and 41BBL can be used to treat cancer.

Disclosed are methods of treating cancer comprising administering to a subject an effective amount of a composition comprising a plasma membrane vesicle comprising at least one NK cell effector agent, wherein the plasma membrane vesicle can be purified from NK cell feeder cells. The NK cell feeder cells can be irradiated autologous or allogeneic peripheral blood mononuclear cells (PBMCs), RPMI8866, HFWT, K562, K562 cells transfected with membrane bound IL-15 and 41BBL), K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

In some aspects, the plasma membrane vesicles used in the methods to treat cancer can be derived from any cell type. The plasma membrane of any cell can be altered to contain the NK cell effector agents of interest.

Disclosed are methods of treating cancer comprising administering to a subject an effective amount of a composition comprising a plasma membrane vesicle comprising at least one NK cell effector agent, wherein an effective amount of the composition comprising a plasma membrane vesicle comprising at least one NK cell effector agent stimulates expansion of NK cells.

Disclosed are methods of treating cancer comprising administering to a subject an effective amount of a composition comprising at least two plasma membrane vesicles, wherein the plasma membrane vesicle comprises at least one NK cell effector agent. The at least two plasma membrane vesicles can comprise the same or different NK cell effector agents. For example, the methods of treating cancer can include administering a composition that comprises a plasma membrane vesicle comprising a membrane bound cytokine and a plasma membrane vesicle comprising a membrane bound NK cell activating agent. In some aspects, methods of treating cancer can comprise administering two or more separate compositions wherein each composition only contains one plasma membrane vesicle.

2. Treating with Membrane Self-Inserting Peptide Conjugates

Membrane self-inserting peptides conjugated to an NK cell effector agent can be used to treat cancer. The membrane self-inserting peptide conjugates can be administered as a peptide conjugate or they can be used to make a composition such as liposomes containing the membrane self-inserting peptide conjugates and then the liposomes can be administered to a subject.

Disclosed are methods of treating cancer comprising administering to a subject an effective amount of a composition comprising a membrane self-inserting peptide conjugated to an NK cell effector agent, wherein an effective amount of the composition comprising a membrane self-inserting peptide conjugated to an NK cell effector agent stimulates expansion of NK cells.

Disclosed are methods of treating cancer comprising administering to a subject an effective amount of a composition comprising a membrane self-inserting peptide conjugated to an NK cell effector agent, wherein the composition can comprise a membrane self-inserting peptide conjugated to IL-15. In some aspects, the composition can comprise a membrane self-inserting peptide conjugated to IL-21. In some aspects, the composition can comprise a membrane self-inserting peptide conjugated to 41BBL. In some aspects the NK cell effector agent is any cytokine, adhesion molecule or NK cell activating agent.

Disclosed are methods of treating cancer comprising administering to a subject an effective amount of a composition comprising a membrane self-inserting peptide conjugated to an NK cell effector agent, wherein the membrane self-inserting peptide can be human Fc, GPI, transmembrane T cell receptor, or pHLIP.

Disclosed are methods of treating cancer comprising administering to a subject an effective amount of a composition comprising a membrane self-inserting peptide conjugated to an NK cell effector agent, wherein the composition comprises at least two membrane self-inserting peptide conjugates, wherein the membrane self-inserting peptide conjugates are conjugated to an NK cell effector agent. The at least two membrane self-inserting peptide conjugates can be conjugated to the same or different NK cell effector agents. For example, the methods of treating cancer can include administering a composition that comprises a membrane self-inserting peptide conjugated to a cytokine and a membrane-self-inserting peptide conjugated to an NK cell activating agent. In some aspects, methods of treating cancer can comprise administering two or more separate compositions wherein each composition only contains one membrane self-inserting peptide conjugate.

3. Combination Treatments

The methods of treating cancer comprising administering to a subject an effective amount of a composition comprising a plasma membrane vesicle comprising at least one NK cell effector agent or a membrane self-inserting peptide conjugated to an NK cell effector agent can be combined with other cancer treatments. For example, the methods can comprise administering to a subject an effective amount of a composition comprising a plasma membrane vesicle comprising at least one NK cell effector agent or a membrane self-inserting peptide conjugated to an NK cell effector agent and a cancer therapeutic.

In some aspects, the cancer therapeutic and the plasma membrane vesicle can be formulated in the same composition. In some aspects, the cancer therapeutic and the plasma membrane vesicle can be formulated in different compositions.

The composition comprising a plasma membrane vesicle comprising at least one NK cell effector agent and the cancer therapeutic can be administered simultaneously or at different times.

Cancer therapeutics that can be administered in combination with the plasma membrane vesicle comprising at least one NK cell effector agent can be any known cancer therapeutics including but not limited to chemotherapeutics and immunotherapeutics, such as but not limited to antibodies and cytokines.

F. Methods of Modulating the Immune System

Disclosed are methods of modulating the immune system comprising administering to a subject one or more compositions, wherein the compositions comprise at least one plasma membrane vesicle comprising an NK cell effector agent or at least one membrane self-inserting peptide conjugated to an NK cell effector agent. In some aspects, the one or more compositions contain a combination of plasma membrane vesicles and membrane self-inserting peptide conjugates.

Disclosed are methods of modulating the immune system comprising administering to a subject one or more compositions, wherein the compositions comprise at least one plasma membrane vesicle comprising an NK cell effector agent or at least one membrane self-inserting peptide conjugated to an NK cell effector agent, wherein modulating the immune system comprises reducing the number of activated T cells, expanding the number of NK cells, reducing the number of dendritic cells, or a combination thereof.

G. Combination Treatments

Disclosed are methods of treating cancer, viral infections, multiple sclerosis and graft-versus-host disease comprising administering to a subject one of the disclosed compositions in combination with a known therapeutic for the disease or disorder being treated. For example, disclosed are methods of treating cancer comprising administering to a subject a plasma membrane vesicle comprising an NK cell effector agent in combination with a known cancer therapeutic such as, but not limited to, a chemotherapeutic, immunotherapeutic, radiation therapy or pain therapeutic.

During combination treatments, the plasma membrane vesicle or membrane self-inserting peptide conjugates disclosed herein can be administered at the same time as the known therapeutic for the disease or disorder being treated. In some aspects, the plasma membrane vesicle or membrane self-inserting peptide conjugates are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days before or after the known therapeutic for the disease or disorder being treated. In some aspects, the plasma membrane vesicle or membrane self-inserting peptide conjugates are administered 1, 2, 3, 4, 5, 6, 7, 8, 9, 10, 11, or 12 months before or after the known therapeutic for the disease or disorder being treated.

H. Administration

The disclosed compositions can be administered in vivo or in vivo. In some aspects, the methods include a combination of in vitro and in vivo administration. The compositions can be administered in vivo in a pharmaceutically acceptable carrier. By "pharmaceutically acceptable" is meant a material that is not biologically or otherwise undesirable, i.e., the material can be administered to a subject, along with the plasma membrane vesicle or membrane self-inserting peptide conjugate, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, by intratumoral injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the plasma membrane vesicles. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the disorder being treated, the particular composition used, its mode of administration and the like. Thus, it is not possible to specify an exact amount for every composition. However, an appropriate amount can be determined by one of ordinary skill in the art using only routine experimentation given the teachings herein.

1. Pharmaceutically Acceptable Carriers

The compositions can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

I. Devices

Disclosed are devices comprising a plasma membrane vesicle comprising an NK cell effector agent. For example, a container used during apheresis can comprise plasma membrane vesicles comprising NK cell effector agents. Thus, during apheresis the cells that pass through the container can be incubated or placed into contact with the plasma membrane vesicles allowing for stimulation of the NK cells and ultimately NK cell expansion.

J. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for preparing the membrane self-inserting peptide conjugates, the kit comprising membrane self-inserting peptides. The kits also can contain reagents used for coupling or conjugating the membrane self-inserting peptide to an NK cell effector agent.

The disclosed kits can also include NK cell effector or expansion agents. The kits can further contain components for preparing plasma membranes or liposomes.

Nanoparticles and microparticles can be provided in the kits.

K. Definitions

It must be noted that as used herein and in the appended claims, the singular forms "a", "an", and "the" include plural reference unless the context clearly dictates otherwise. Thus, for example, reference to "a plasma membrane vesicle" includes a plurality of such plasma membrane vesicles, reference to "the NK cell effector agent" is a reference to one or more NK cell effector agents and equivalents thereof known to those skilled in the art, and so forth.

"Plasma membrane vesicle" refers to a preparation of a plasma membrane from a cell or an artificially made plasma membrane or liposome.

"Membrane self-inserting peptides" are peptides that are capable of inserting or anchoring to a cell membrane.

"Membrane self-inserting peptide conjugates" are membrane self-inserting peptides conjugated or coupled to an NK cell effector agent.

"NK cell effector agents" are agents that cause proliferation, stimulation, adhesion to or activation of NK cells. NK cell effector agents can be cytokines, adhesion molecules or NK cell activating agents.

"NK cell activating agent" refers to stimulatory ligands that bind to activating receptors present on the surface of NK cells.

"Modulate" or "modulating" as used herein refers to an increase or decrease. Modulating results in any difference compared to normal immune function. Thus, modulating the immune system refers to increasing or decreasing immune cells.

"Optional" or "optionally" means that the subsequently described event, circumstance, or material may or may not occur or be present, and that the description includes instances where the event, circumstance, or material occurs or is present and instances where it does not occur or is not present.

As used herein, the term "subject" refers to any organism to which the disclosed compositions can be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals). Typically, "subjects" are animals, including mammals such as humans and primates; and the like. Subjects can also refer to a cell or a cell line.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a membrane self-inserting peptide conjugate is disclosed and discussed and a number of modifications that can be made to a number of molecules including the membrane self-inserting peptide conjugate are discussed, each and every combination and permutation of the membrane self-inserting peptide conjugate and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

Figure 3:
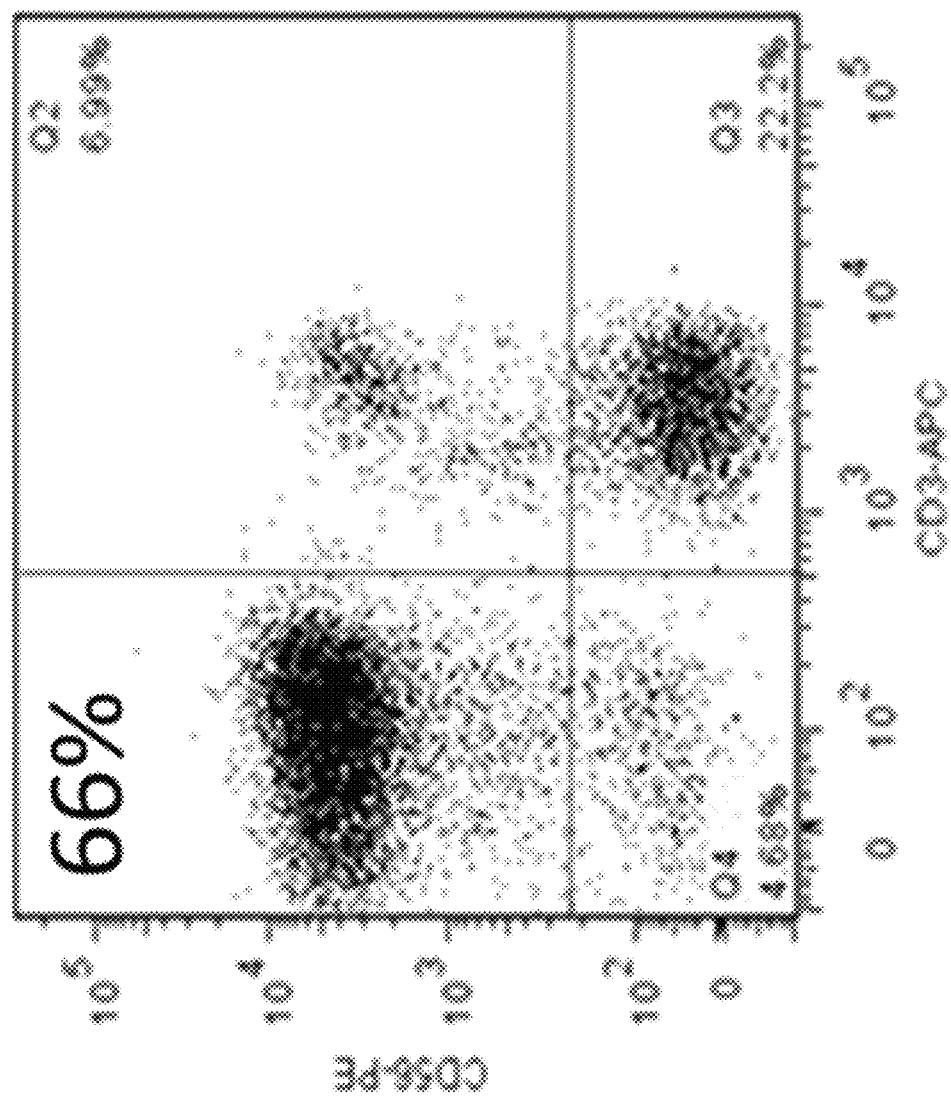
FIG. 3 presents dot plots of CD56-PE vs. CD3-APC, showing CD56+CD3− NK cell population increases as the concentration of K562-mb21 plasma membrane in culture increases after 10 days.
Figure 3:
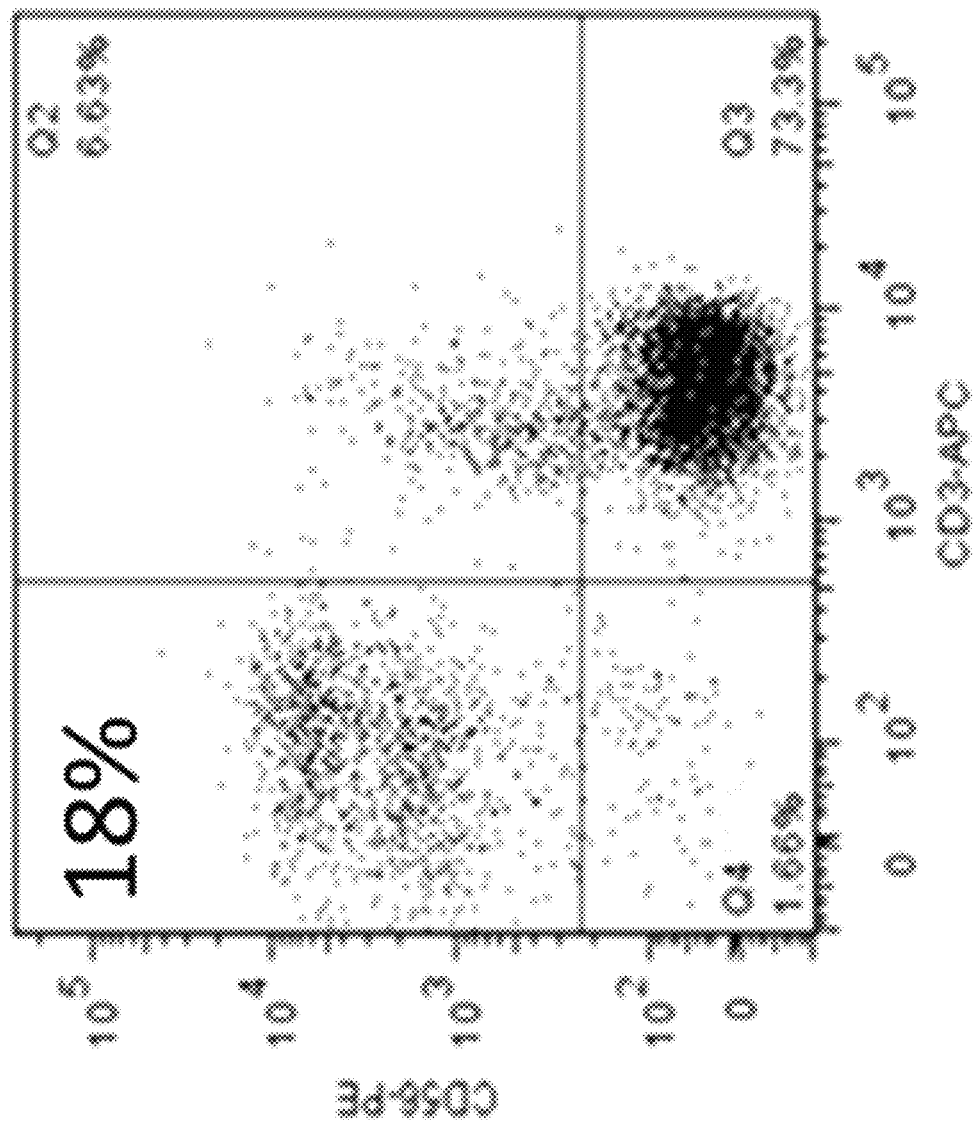
Figure 3:
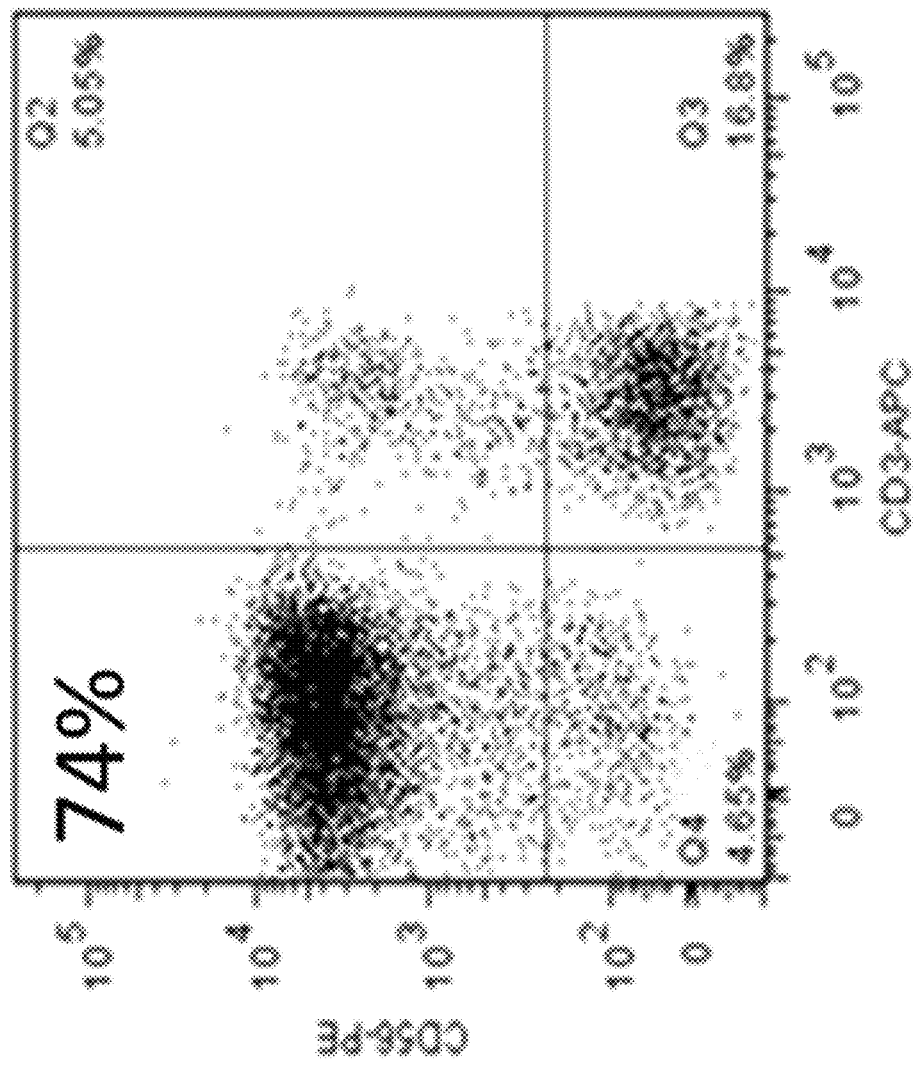
Figure 3:
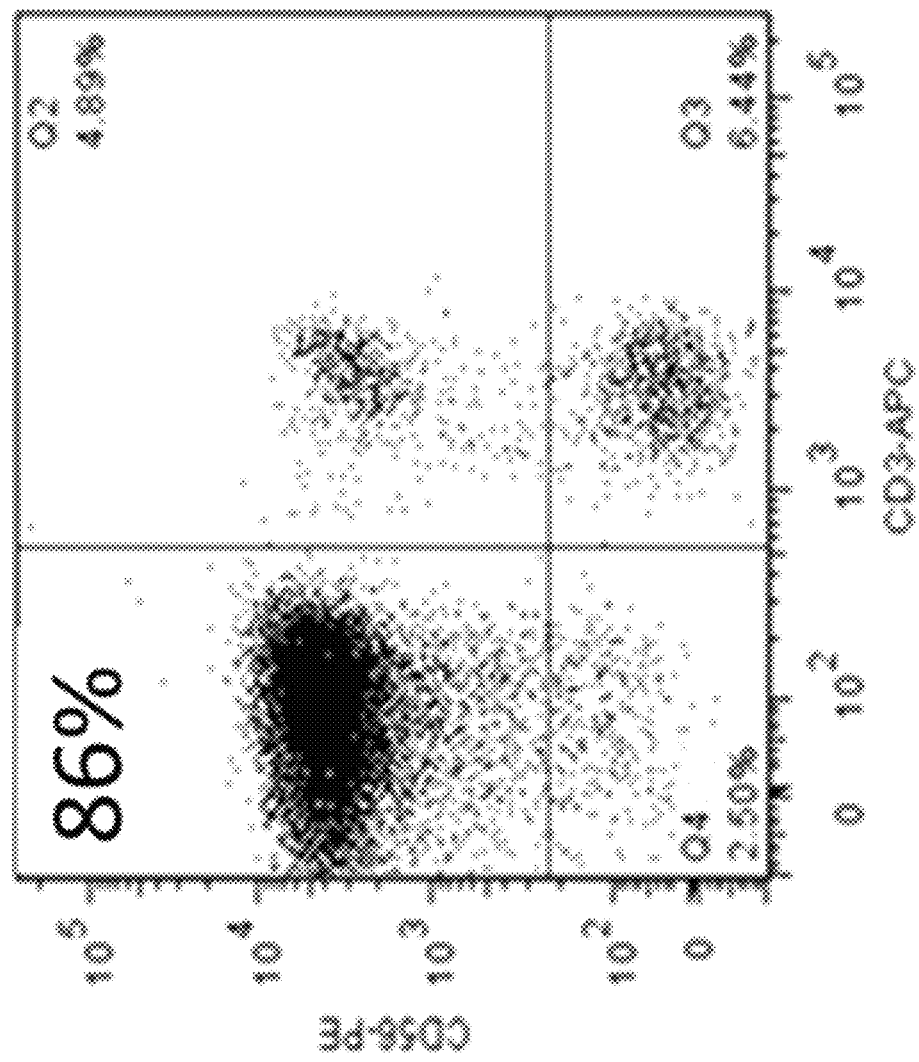
Figure 4:
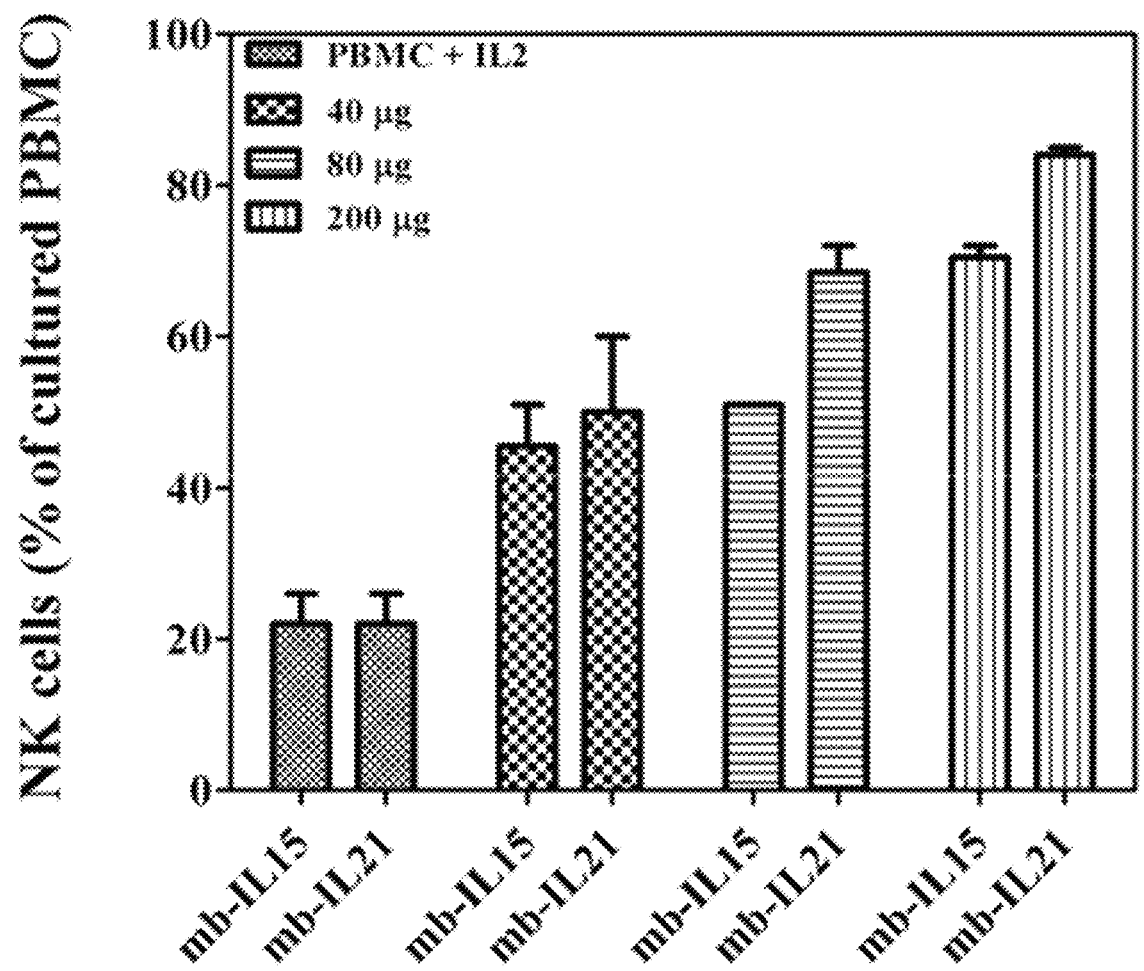
FIG. 4 presents a bar graph depicting the increase in NK cell percentage in cultured cells resulting from an increase in concentration of K562-mb15 or K562-mb21 plasma membrane.
Figure 5:
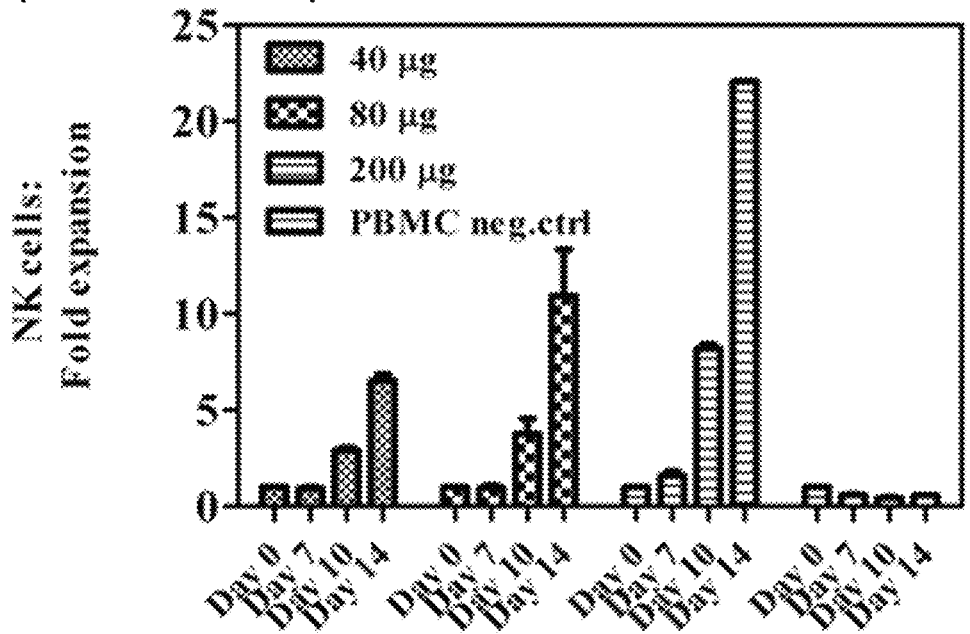
FIG. 5 presents bar graphs showing an increase in NK cell expansion with increasing concentrations of PM-mb15-41BBL or PM-mb21-41BBL membrane vesicles in culture.
Figure 5:
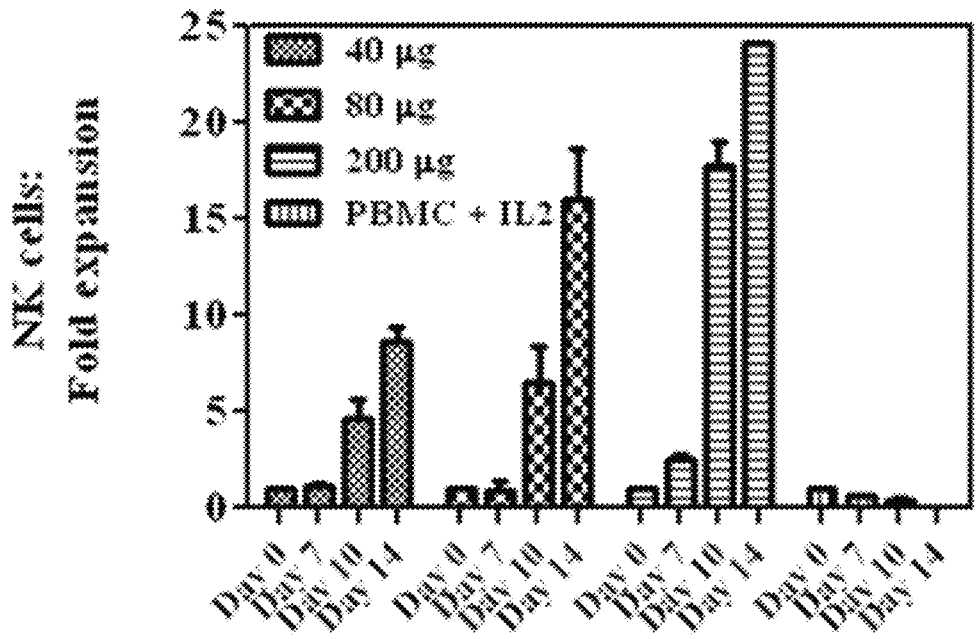

A. Example 1: In Vive Generation of Cytotoxic Natural Killer Cells and Associated Cancer Treatment Methods The expansion of NK cells can occur by using membrane vesicles derived from stimulator cells. K562-mb15-41BBL and K562-mb21-41BBL stimulator cells were selected for generation of plasma membrane (PM) vesicles because these cells were reported to expand NK cells very robustly and do not require the isolation of NK cells from peripheral blood mononuclear cell (PBMC) mixture prior to culture initiation. Furthermore, the presence of stimulatory ligands 41BBL and mbIL15 or mbIL21 can be easily tracked by antibody staining to confirm expression of these molecules on the feeder cells and their presence in isolated membrane vesicles as well as on membrane coated microparticles. Whether or not particles consisting of purified membrane vesicles derived from stimulator cells support expansion of NK-cells in a similar fashion as the stimulator cells do was tested. When PBMCs were exposed in culture to 50 U/mL of IL-2 and increasing concentrations of PM-mb15-41BBL or PM-mb21-41BBL vesicles over 10 day period the NK cells content in the PBMC mixture increased proportionally to the PM concentration used (FIGS. 3 and 4). At the highest concentration of 200 µg/mL of plasma membrane proteins tested, the resulting NK cell content was 70% and 82% in presence of PM-mb15-41BBL or PM-mb21-41BBL respectively. For comparison, the NK cells comprised only 22% of cellular content of the cultures that were exposed to IL-2 only. Furthermore, the total NK cell number increased in the cultures that were exposed to PM vesicles and the increase was proportional to the PM concentration used. Thus, NK cell expansion was the highest in the cultures that received IL-2 with 200 µg/mL of plasma membrane proteins where NK cells expanded 24 and 22 fold over 14 days in the presence of PM-mb21-41BBL or PM-mb15-41BBL vesicles respectively while no expansion was observed in the control culture (FIG. 5). Thus, both the level of expansion and content of NK cells in the culture were directly proportional to the concentration of membrane particles used (FIGS. 3, 4 and 5). Although the level of expansion in the presence of PM particles was lower than that observed in the control cultures where NK cells expanded by 88 and 150 fold in the presence of live K562-mb15-41BBL and K562-mb21-41BBL, respectively this expansion is sufficient to generate the required doses for clinical applications. Thus, these experiments indicate that NK cells can be selectively expanded within PBMC mixture using particles consisting of purified plasma membrane vesicles with stimulatory ligands without feeders.

Figure 6:
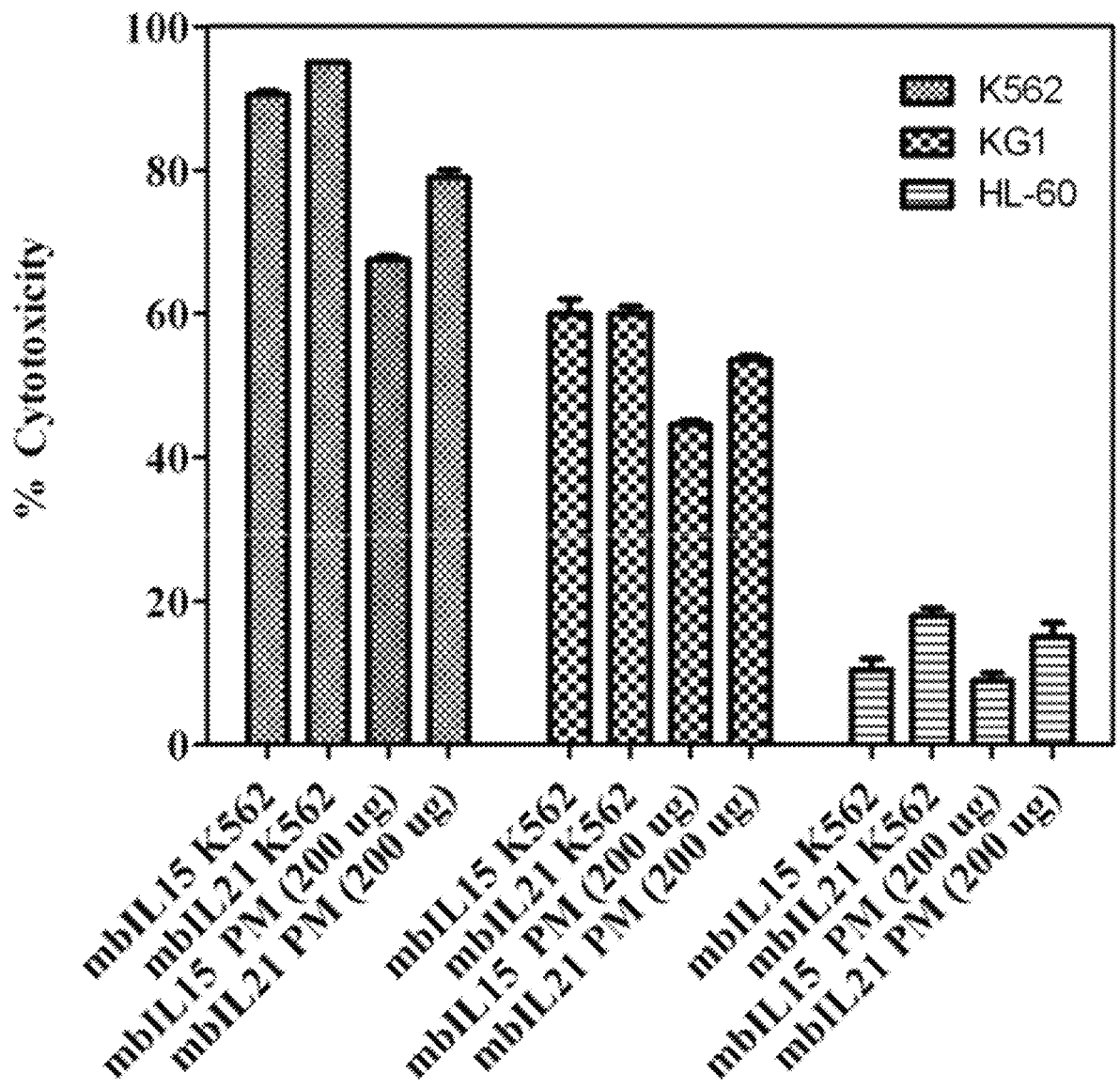
FIG. 6 presents a bar graph showing the percent cytotoxicity of mbIL15 K562, mbIL21 K562, mbIL15 PM, or mbIL21 PM against K562, KG1, and HL-60 cells at day 10 of culture. NK cells expanded with plasma membrane from K562mb15 and K562mb21 elicit comparable cytotoxic responses against AML (KG1 and HL-60) and CML (K562) cell lines when compared to live feeder cell cultured NK cells.

NK cells expanded by culturing for 14 days with 200 µg/mL PM-mb15-41BBL or PM-mb21-41BBL membrane vesicles were tested for cytotoxic function at a 1:1 (E:T) ratio against chronic myeloid leukemia (CML) cell line K562, and acute myeloid leukemia (AML) cell lines KG1 and HL-60. Level of cytotoxicity was compared to NK cells cultured with K562-mb15-41BBL or K562-mb21-41BBL live feeder cells (FIG. 6). NK cells stimulated with PM-mb15-41BBL and PM-mb21-41BBL killed 60 and 78% of K562 target cells, 44% and 54% of KG1 cells and 9 and 15% of HL-60 respectively. These levels of cytotoxic response observed with PM stimulated NK cells were only slightly lower than those observed with NK cells cultured for 14 days using the live K562-mb15-41BBL or K562-mb21-41BBL feeder cell lines. These results indicate that NK-cells expanded using PM-mb15-41BBL are cytotoxic against acute myeloid leukemia targets and thus are suitable for therapeutic applications in cancer treatment.

Together these results indicate that NK cells can be selectively expanded within the PBMC mixture cells using membrane vesicles containing stimulatory ligands and in the absence of feeder cells. These cells are cytotoxic against various leukemia derived targets. This method of expansion is amenable for both in vitro and in vivo expansion of NK cells for clinical applications. The suitability of membrane particles for use in in vivo expansion is demonstrated by the increased NK cell number in patients treated with dendritic cell derived exosomes (Dex) cancer vaccine-membrane particles naturally secreted by dendritic and other immune cells (Viaud, Terme et al. 2009).

Figure 7:
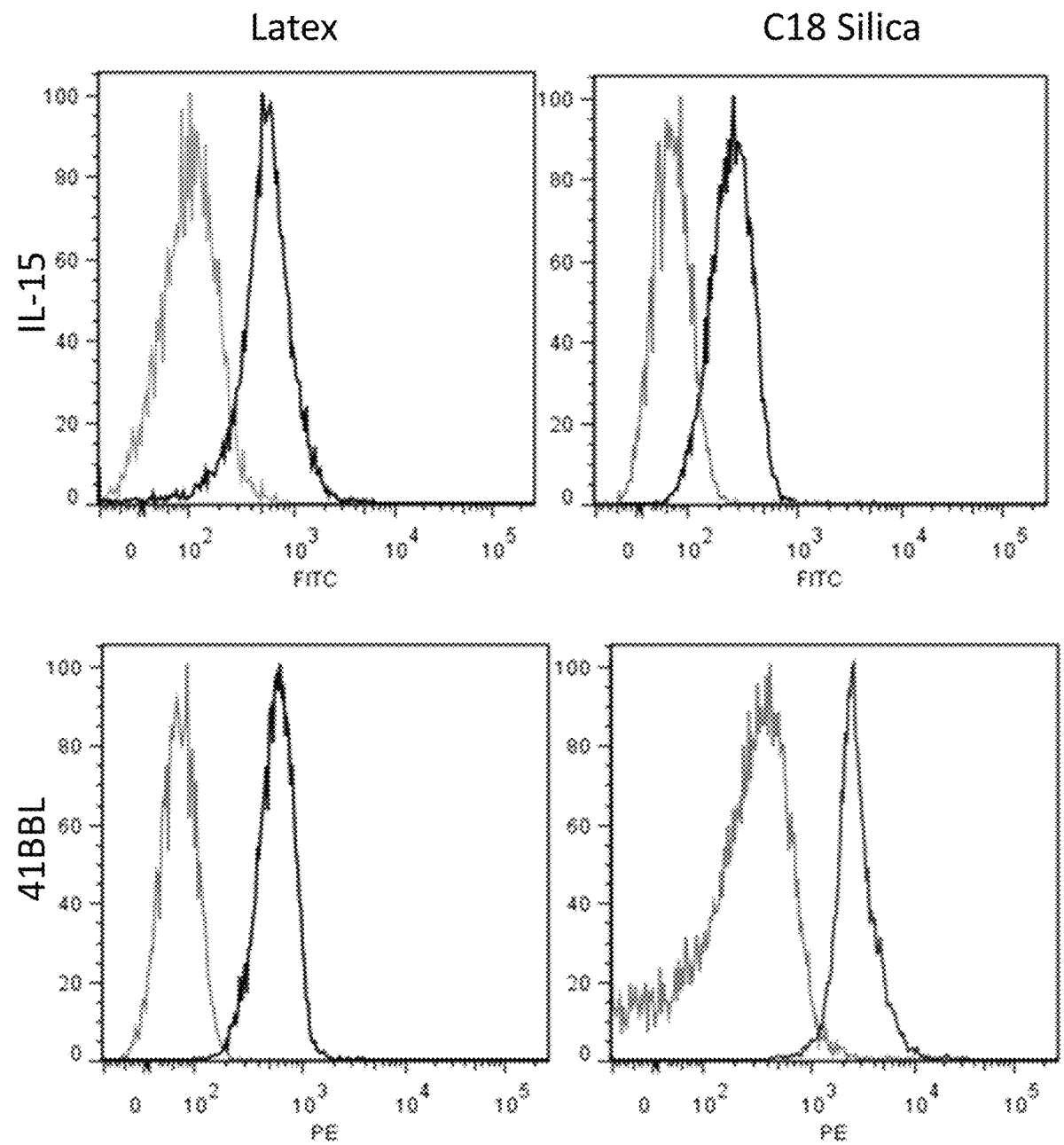
FIG. 7 presents histograms showing IL-15-FITC and 41BBL-PE. Latex or C18 Silica beads were coated with K562mb15 plasma membrane containing membrane-bound IL15 and 41BBL. Both latex and C18 Silica beads showed the presence of IL-15 and 41BBL after coating. Isotype is the lighter colored line.

FIG. 7 shows the generation of latex particles coated with PM-mb15-41BBL membranes. FIG. 7 depicts histograms showing IL15-FITC (top) and 41BBL-PE (bottom). Latex (left) or C18 Silica (right) beads were coated with K562mb15 plasma membrane containing membrane bound IL-15 and 41BBL. Both latex and C18 Silica bead showed presence of IL-15 and 41BBL after coating (Isotype in grey). To prepare the membrane-coated latex particles, plasma membrane vesicles purified as described and containing the stimulatory molecules 41BBL and mbIL15 were used and were embedded on 5 micrometer latex microparticles using a previously established protocol. Sulfate polystyrene latex microspheres (Inerfacial Dynamics) were resuspended in PBS, washed, and counted on a hemocytometer. To coat the beads, an aliquot of bead suspension was added to PM-mb15-41BBL membrane solution while sonicating the suspension. The bead-membrane solution was placed on a rotator at 4 degrees C. for 2 hours. Beads were centrifuged and washed three times. The beads were labeled with antibodies and analyzed by flow cytometry to confirm the presence of stimulatory proteins on the surface of the beads (left panels). Beads coated with membrane showed positive staining for both IL-15 and 41BBL and low background staining with isotype control antibodies. C18-silica beads were coated with PM-mb15-41BBL in a similar fashion. Again, the presence of stimulatory molecules was confirmed by antibody staining (right panels). These results indicate that particles coated with cellular membranes containing stimulatory molecules can be generated.

FIG. 8 depicts debris found in cultures after NK cell expansion. a) FSC vs. SSC of PBMC (red) together with plasma membrane at day 10 of culture. b) FSC vs. SSC of PBMC (red) together with K562mb15 feeder cell debris (green). The top and bottom figures represent separate cultures on day 10. The top figure has significantly more feeder cell debris vs. the bottom figure.

1. Materials and Methods

The cell lines K562-mb15-41BBL and K562-mb21-41BBL (K562-clone9.mbIL21) were used. K562, KG1 and HL-60 cell lines used in cytotox assays were purchased from the American Tissue Culture Collection (ATCC).

Analysis were performed with the following mouse monoclonal antibodies: CD56-PE (Miltenyi Biotech), CD3-APC, CD16-FITC (Beckman Coulter), CD19-PECy7, 41BBL-PE (BD Biosciences) and 41BBL (R&D).

Other reagents and kits used include sulphate latex beads (5 μm; Invitrogen), C18-silica beads (10 μm; Sorbtec), RPMI media (Thermo Scientific), CellGro media (Cellgenix) Fetal bovine serum (Invitrogen), IL-2 (Peprotec), Glutamax (Invitrogen). [0052] The preparation of PM-mb15-41BBL and PM-mb21-41BBL plasma membrane vesicles was performed as follows. K562-mb15-41BBL and K562-mb21-41BBL were cultured in RPMI media supplemented with $10^0$/FBS and the culture was scaled up to IL. Cells were harvested by centrifugation at 1000×g, washed with cold PBS with 10 mM EDTA and resuspended in lysis buffer (50 mM HEPES, pH 7.4, protease inhibitor cocktail). Cells were disrupted with Dounce homogenizer and the solution was spun down at 300×g for 15 minutes to remove any remaining whole cells. The crude plasma membranes were separated from the cytosolic components by centrifugation for 30 min at 4° C. (30000 rpm, 50Ti). The crude membranes were resuspended in lysis buffer and further purified using a sucrose density gradient to yield pure plasma membrane vesicles, referred to as PM-mb15-41BBL or PM-mb21-41BBL. A BCA assay was used to determine the membrane protein concentration while the amount of stimulatory 41-BBL ligand was determined by Western blotting.

NK cell expansion within PBMC mixture was tested in the presence of increasing concentrations of PM-mb15-41BBL or PM-mb21-41BBL membrane particles. The amounts used were 40, 80, and 200 μg of membrane protein per 1 mL of culture which for PM-mb15-41BBL culture corresponded to 16, 32, 80 ng of 41-BBL protein per mL of culture. PBMCs isolated from blood by Ficol-Paque density gradient were grown in SCGM Cell Gro media supplemented with 10% FBS and 10 or 50 U/mL of IL-2 and increasing concentrations of membrane particles. Cells were maintained at 37° C. in a humidified atmosphere with 5% $CO_2$. Starting on day 5 of culture media were exchanged every other day by replacing half of the media with fresh media as well as replacing the amount of membrane removed through media replacement. Cells were counted every other day and the culture content was checked on days 7, 10 and 14.

Cytotoxicity assays were performed as follows. Leukemia derived target cell lines K562, KG1, HR-60R were labeled with TFL4 (Oncoimmunin) or CellTrace Far Red (CTFR; Invitrogen), a far-red-fluorescent tracer for long-term cell labeling, prior to addition of effector NK cells. Cells were washed twice with PBS buffer with 1% BSA.

Target cells were then co-incubated with various amounts of NK-cells for 90 minutes at 37° C. in the humidified atmosphere Air/$CO_2$ 95/5%. At the end of co-incubation cells were transferred to tubes, placed on ice and loaded with caspase/granzyme substrate (Pantoxilux kit, OncoImmunin) and labeled with antibodies against surface antigens. Cells were immediately analyzed by flow cytometry (BD FACS Canto-II). The NK cell-induced cell death was detected using cell-permeable fluorogenic caspase/granzyme substrate (OncoImmunin). Cleavage of this substrate by granzyme, released into the target cell upon interaction with NK-cells, and downstream caspase produces green fluorescence inside dying target cells.

B. Example 2: Optimization of Plasma Membrane Vesicles for Expanding NK Cells

1. SUMMARY

Methods of preparing plasma membrane vesicles have been optimized as well as methods of increasing the level of expansion of NK cells in the presence of the vesicles. NK cells expanded with these methods were determined to kill primary leukemia cells from patients. The procedure was scaled up for culturing K562-mb15-41BBL cells and optimized preparation of plasma membrane (PM) vesicles by disrupting cells using nitrogen cavitation method. Optimized plasma membrane vesicles were more homogenous and had higher levels of stimulatory ligand 41BBL. In the NK cell expansion tests with PBMC derived from healthy donors (n=3) as starting material, the optimized PM vesicles outperformed previous preparations of PM in stimulating NK cell growth and yielded levels of selective NK cell expansion that are comparable to those attained with live K562-mb15-41BBL feeder cells. The NK cell surface expression of a multitude of surface markers with relevance to NK cell function were determined in the staring material as well as in NK cells expanded in presence of either PM vesicle or live feeder cells. The initial analysis indicated that the NK cells expanded with PM have similar activated phenotype to those expanded with live K562-mb15-41BBL feeders cells yet significantly altered from the resting state phenotype as measured with cells freshly isolated from peripheral blood. The function of freshly isolated and expanded NK cells were tested by measuring the cytotoxicity levels against both leukemia cell lines (K562, KG1, HL-60, BDCM) and primary leukemia blasts (from 3 different patient AML samples) at varying effector to target ratios. The data indicate that NK cells expanded by stimulation with PM-mb15-41BBL vesicles kill cell lines and primary AML cell and do it more efficiently than freshly isolated NK cells. In vivo testing in NSG of the NK cell expansion with PM has been performed and found that NK cells can be expanded directly in vivo in the animal with serial dosing of PM vesicles.

2. RESULTS

Figure 9:
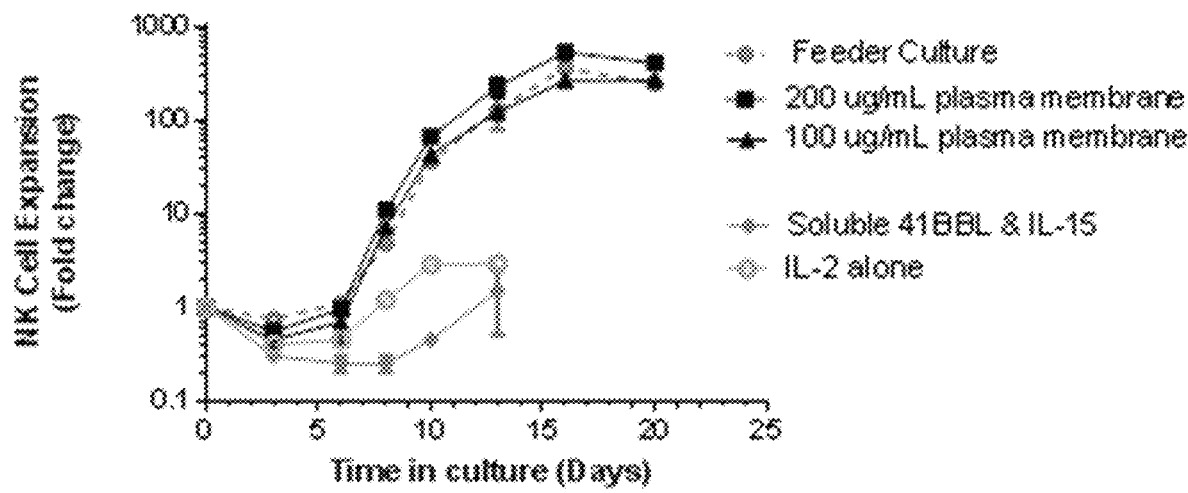
FIG. 9 shows that PM-mb15-41BBL vesicles efficiently expand NK cells. PBMC were co-cultured with K562-mb15-41BBL feeders or were stimulated with PM-mb15-41BBL vesicles (at 100 or 200 μg of membrane protein/ml) for 21 days. The cell content was tested every 2-3 days and media were exchanged as needed. The figure depicts one representative expansion out 3 performed with PBMCs derived from 3 different donors. Each point represents average of duplicate cultures.
Figure 10:
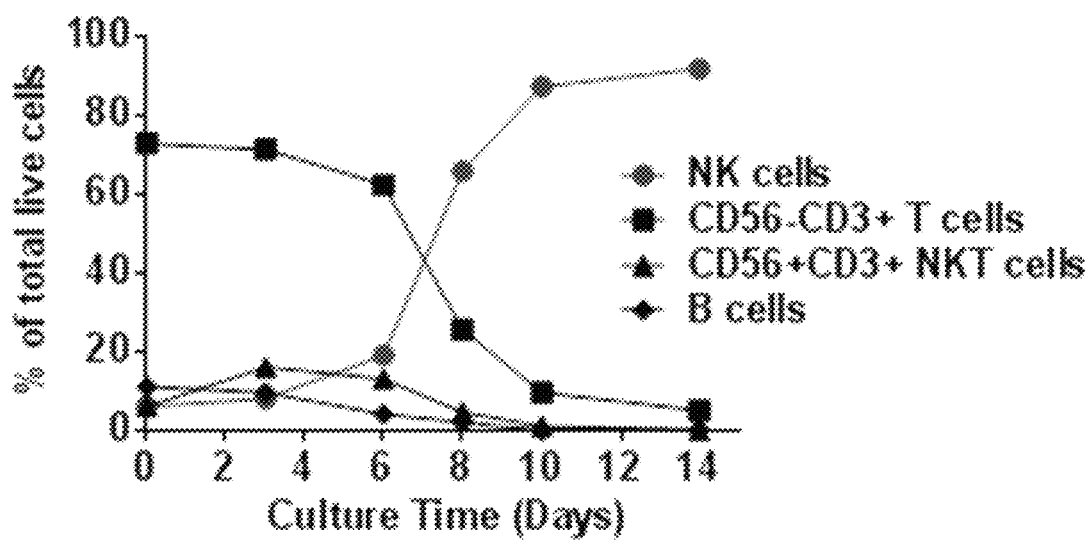
FIG. 10 shows that PM-mb15-41BBL vesicles selectively expand NK cells. PBMC were stimulated with PM-mb15-41BBL vesicles at 200 μg of membrane protein/ml for 14 days. The cell count and content was tested every 2-3 days by staining the cells with anti-CD56-PE and anti-CD3-APC antibodies and analyzing the content on an Accuri flow cytometer. In all experiments performed to date CD56+ CD3− NK cells selectively expanded within PBMCs when stimulated with PM-mb15-41BBL vesicles and by day 14th consisted >95% of the cellular content. The figure depicts one representative expansion out of 3 performed with PBMCs derived from 3 different donors.
Figure 11:
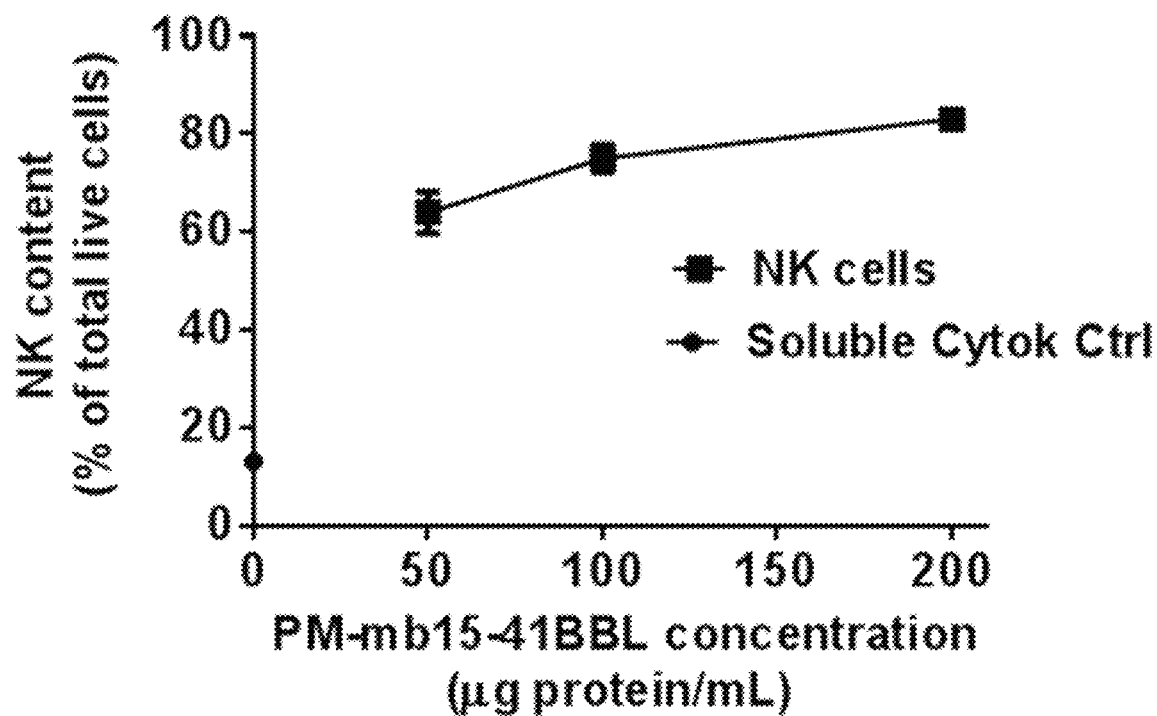
FIG. 11 shows that NK cell content increases with the concentration of PM-mb15-41BBL vesicles. PBMC were stimulated with varying amounts of plasma membrane vesicles for 14 days. Cell content measured using anti-CD56-PE and anti-CD3-APC. Each point represents average of duplicate cultures.
Figure 12:
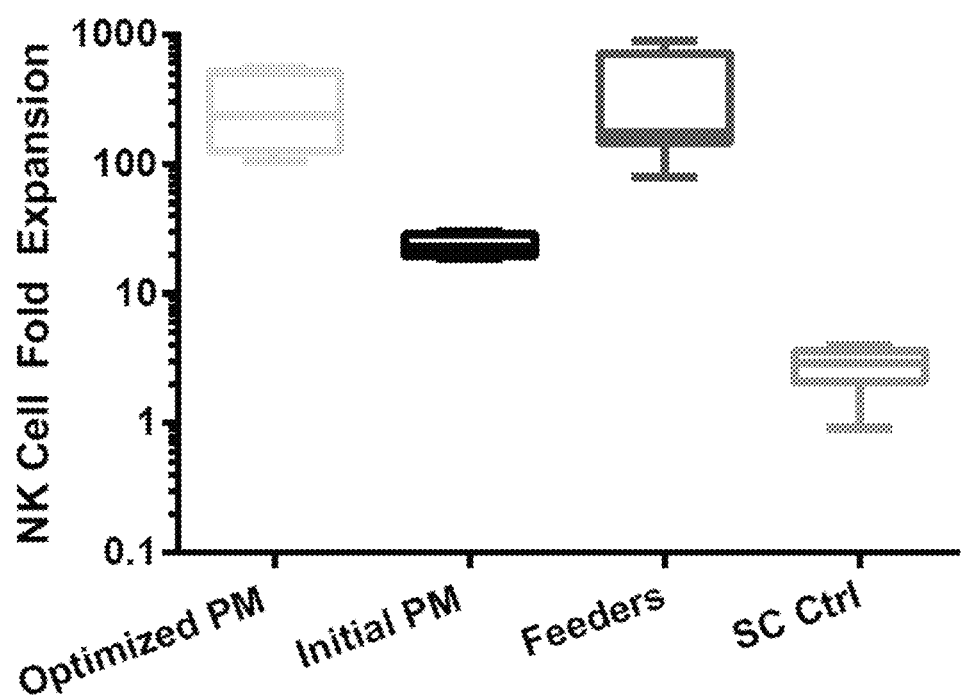
FIG. 12 shows that optimized PM-mb15-41BBL vesicles expand NK cells equally well as live feeder cells. PBMC were co-cultured with optimized (n=6) or initial (n=4) PM vesicle preparations at 200 μg of membrane protein/mL or were co-cultured with 1×10$^6$/mL K562-mb15-41BBL live feeders (n=6, Feeders positive ctrl) or 50 ng/mL soluble IL-15 and 50 ng/mL soluble 41BBL (n=6, SC Ctrl) for up to 20 days. The plot depicts the fold of NK cell expansion after 12-13 days in culture.
Figure 13:
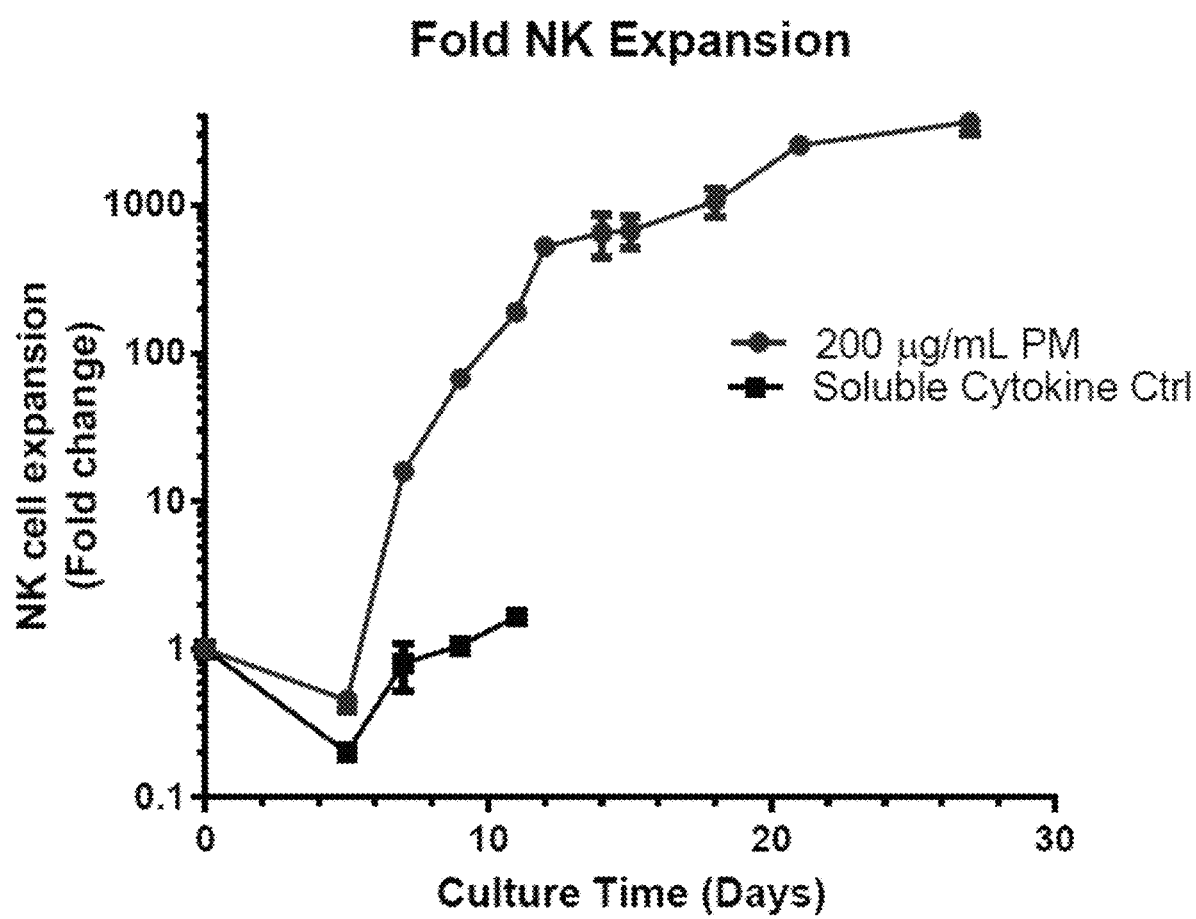
FIG. 13 shows the growth rate of PM-mb15-41BBL vesicles expanded NK cells slows down after two weeks in culture. PBMC were co-cultured with PM vesicles at 200 μg of membrane protein/mL for over 4 weeks. ½ of media was replaced every other day after day 3. 100 μg of PM vesicles was replaced with the media replacement every other day. Cell content measured using anti-CD56-PE and anti-CD3-APC. Each point represents average of duplicate cultures. The figure depicts one representative expansion out of 3 performed with PBMCs derived from 3 different donors.
Figure 14:
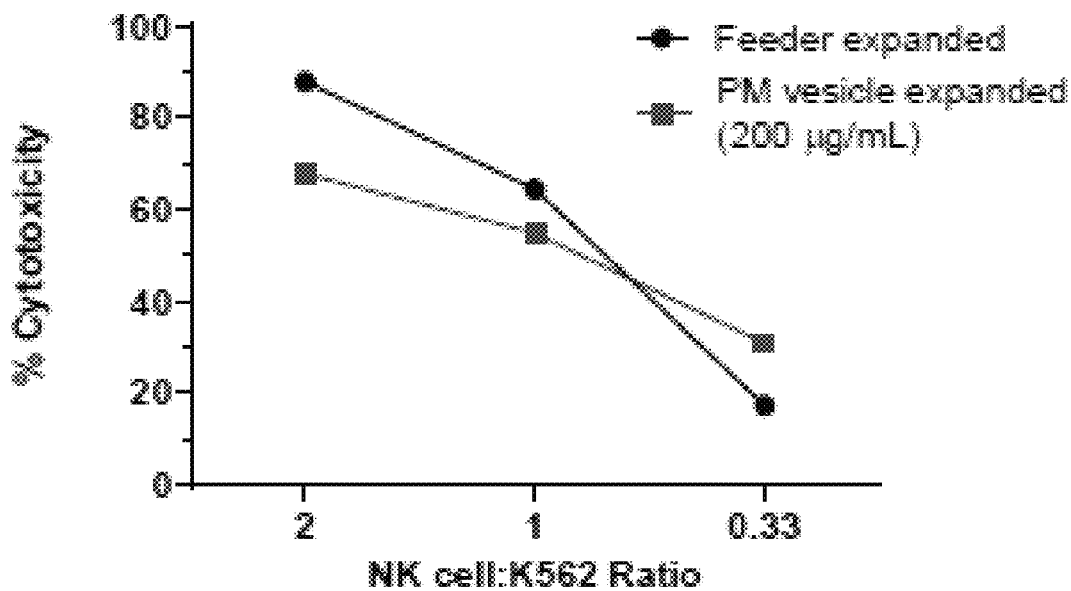
FIG. 14 shows PM-mb15-41BBL vesicles expanded NK cells are cytotoxic against CML and AML targets. Cytotoxicity assay performed on day 13-14 using PanToxiLux kit measuring Caspase/Granzyme activity in labeled target cells. Target cells at $0.5 \times 10^6$/mL were co-incubates with expanded NK cells at varying ratios in duplicate for 1.5 hours and then analyzed by flow cytometry. The amount of spontaneous target cell death was determined using a "Target Alone" control. Percent cytotoxicity was determent by subtracting spontaneous cell death from target cell death and then dividing by total target cells. Figure depicts one representative cytotox assay out of 3 performed with PBMCs derived from 3 different donors.
Figure 14:
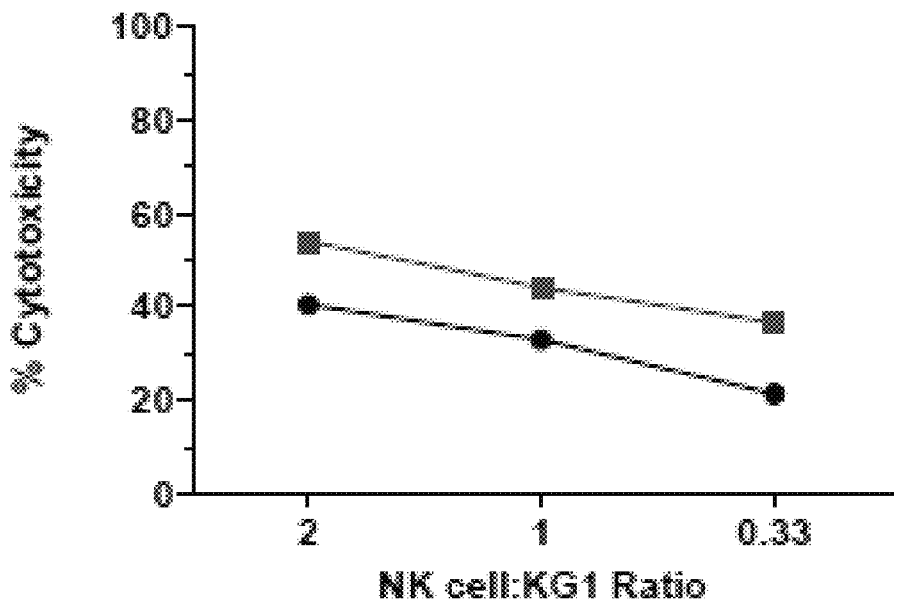
Figure 14:
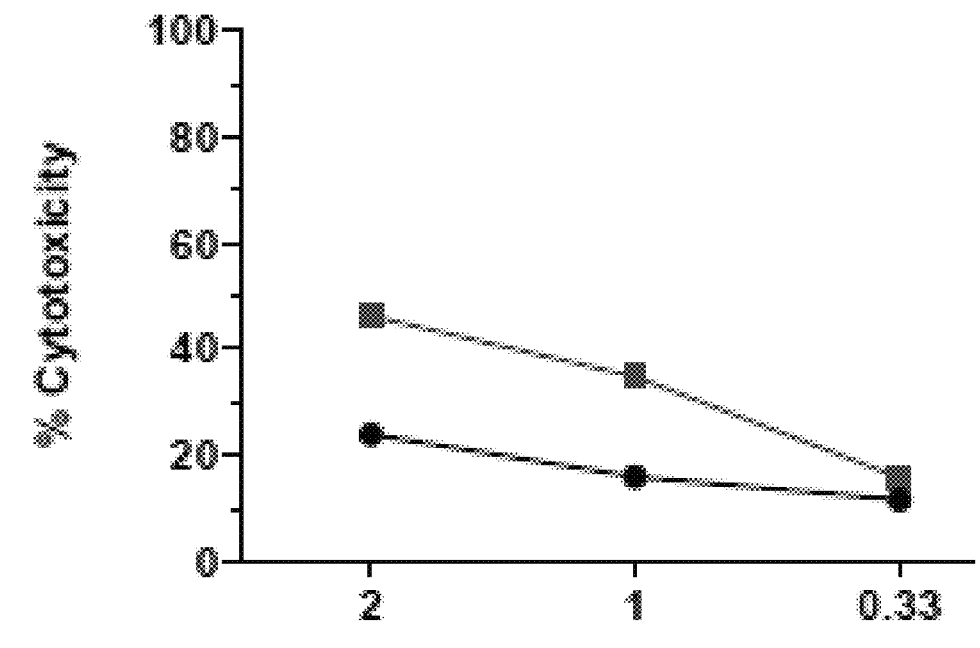
Figure 14:
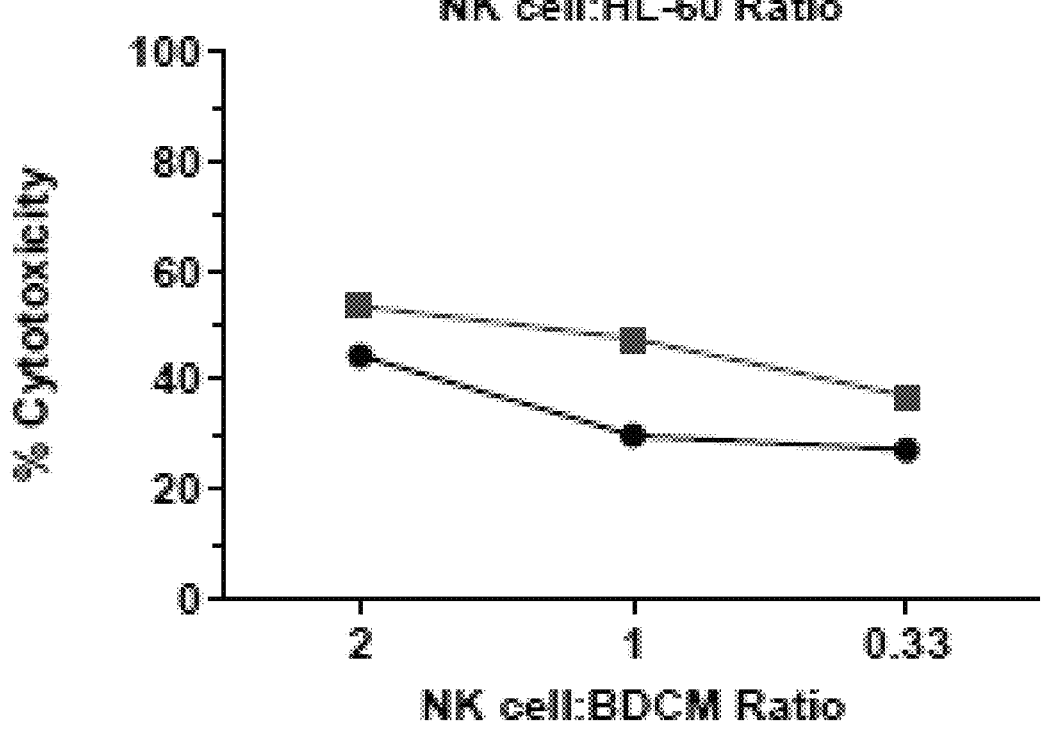
Figure 15:
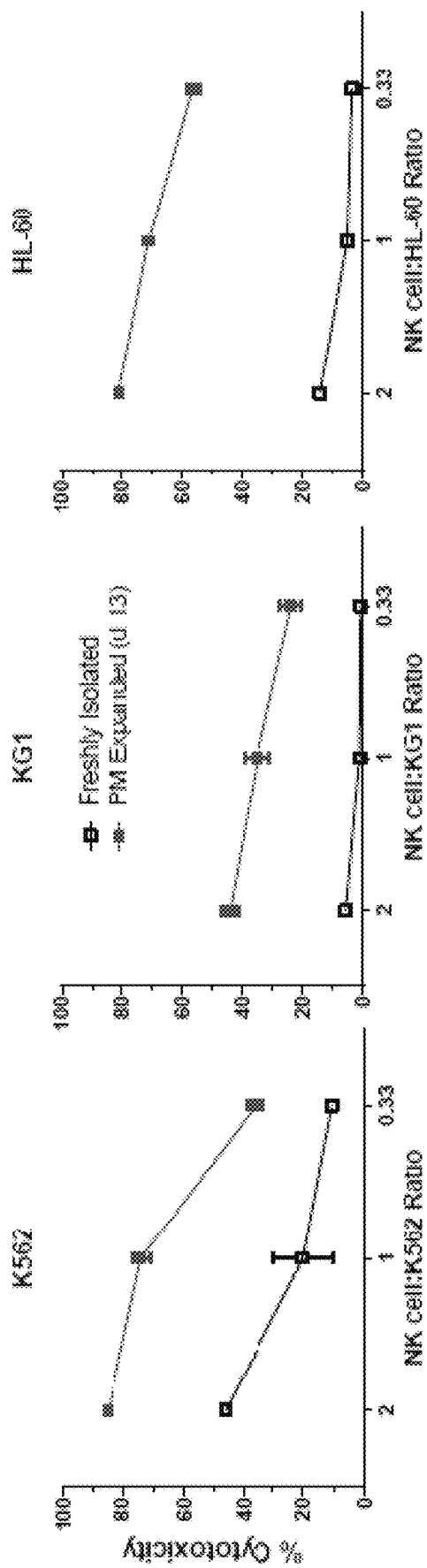
FIG. 15 shows PM-mb15-41BBL vesicles expanded NK target cells as compared to freshly isolated NK cells. Initial cytotoxicity assay performed on freshly isolated NK cells from healthy donors. NK's isolated from PBMC after Ficoll using Stem Cell Technologies Negative Selection kit were allowed to rest and pre-activate overnight in growth media+ FBS+high (1000 U/mL) IL2 before testing cytotoxicity. NK's expanded from PBMC with PM vesicles at 200 μg of membrane protein/mL for 13-14 days were pre-activated with high (1000 U/mL) IL2 overnight before testing cytotoxicity. The figure depicts one representative expansion out of 3 performed with PBMCs derived from 3 different donors.
Figure 16:
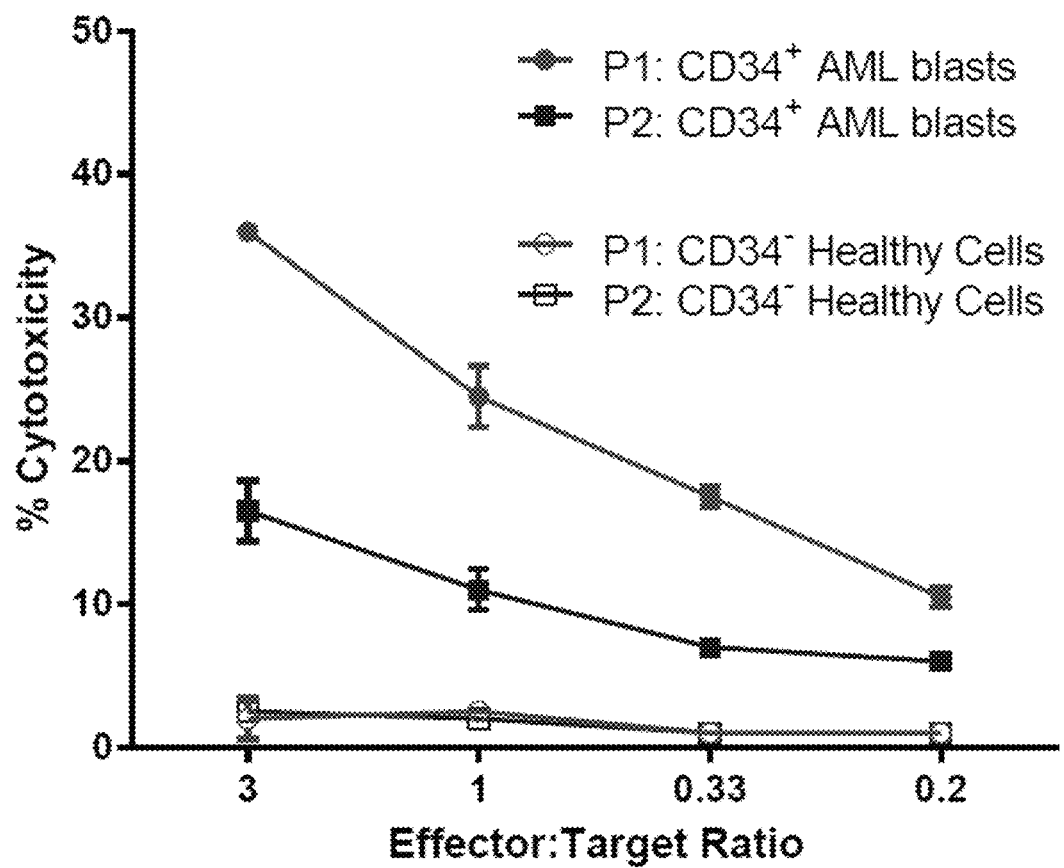
FIG. 16 shows PM-mb15-41BBL vesicles expanded NK cells are cytotoxic against patient primary AML cells. Cytotoxicity of NK cells cultured with PM vesicles at 200 μg of membrane protein/mL for 13-14 days were tested against primary tumor from 2 different patients. Tumor cells were collected from bone marrow or peripheral blood of patients that signed informed consent. Leukemia blasts were separated by Ficoll gradient and cryopreserved for future experiments. Thawed tumor samples were incubated in media overnight to recover before using in cytotox assays. Target tumor cells were stained with TFL4 dye to distinguish from effectors. Additionally, tumor cells were stained with anti-CD34-PE to distinguish patient tumor cells from healthy patient PBMC. The figure depicts one representative expansion out of 3 performed with PBMCs derived from 3 different donors.
Figure 17:
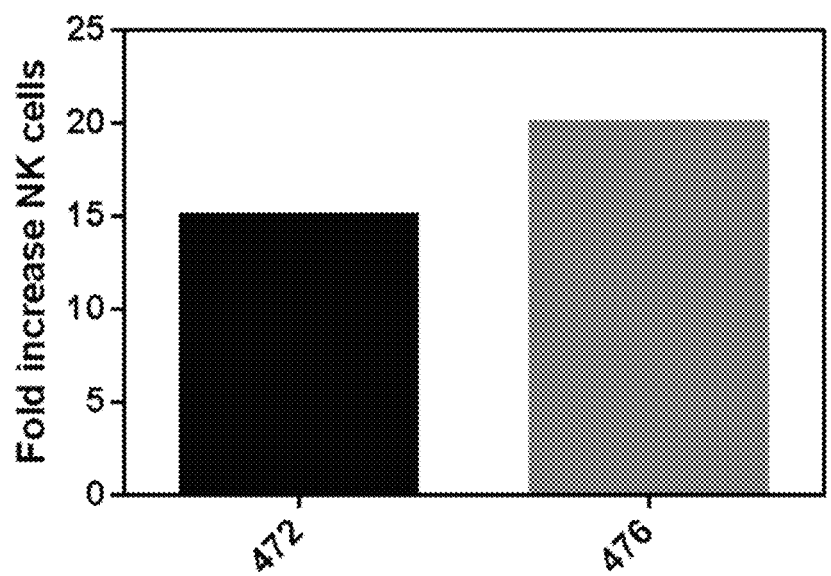
FIG. 17 shows PM-mb15-41BBL vesicles expand NK cells in vivo in NSG mice. PBMC derived from two different donor were stimulated with PM-mb15-41BBL vesicles at 200 μg of membrane protein/ml for 7 days. On day seven cells were counted and analyzed for cell content, spun down, resuspended at 15 mln NK cells/mL in 100 μL of clear RPMI with 50 U/mL of IL 2 and injected into the tail vain of NSG mouse. Mice were injected 3 times a week with PM-mb15-41BBL vesicles (200 μg of membrane protein/ml) and low 100 U or 1000 U dose of IL-2. On day 1 and 4 post injection 50-100 μL of mouse blood was drawn and analyzed for presence and number of human CD45+ lymphocytes, CD3–CD56+ NK cells and CD3+CD56– T cells. The graph represents fold expansion of NK cells between days 1-3 post injection.

NK expansion has been tested from four different healthy donors using PM-mb15-41-BBL vesicle from the optimized plasma membrane preparations. The optimized PM-mb15-41-BBL vesicle efficiently and selectively expands NK cells within the PBMCs mixture and the NK cell content increased with the increasing amounts of PM vesicles (FIGS. 9, 10, and 11). The NK cell numbers increased on average 293 fold (range 104-557) after 12-13 days of culture in the presence of the optimized PM vesicles and 173 fold (79-895) in presence of live feeder cells (FIG. 12). This represents a significant improvement in the levels of NK cell expansion attained with the optimized PM vesicle over the initial preparations (233 vs. 23 respectively). The NK cells growth rate stimulated with PM vesicles changes over the 28 day culture time period with the exponential phase occurring between days 5 and 14 of culture after which the growth slows down (FIG. 13). Significant progress has been made in accessing the cytotoxicity of the NK cells that were expanded using PM vesicle. NK cells expanded using optimized PM-mb15-41-BBL vesicles killed all tested leukemia target cell lines as efficiently as NK cells expanded using live K562-mb5-41-BBL feeder cells (FIG. 14) and were significantly more cytotoxic as compared to freshly isolated NK cells (FIG. 15). Moreover, NK cells expanded with PM vesicle efficiently killed patient derived CD34+ AML blasts while sparing healthy CD34− cells (FIG. 16). In humanized NSG mouse animal model, NK cells preincubated for 7 days with PM-mb15-41-BBL vesicle and injected i.v. and further stimulated with PM-mb15-41-BBL vesicle delivered i.v. 3× weekly (M,W,F) along with low doses of IL-2 increased in numbers 15-20 fold over 3 day period (FIG. 17) while control cells expanded under optimal culture condition expended only 8 times over the same time period.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

We claim:

1. A method of treating cancer comprising administering to a subject an effective amount of a composition comprising a membrane self-inserting peptide conjugated to an NK cell effector agent, wherein the NK cell effector agent is selected from the group consisting of IL-15, IL-2, IL-12, IL-18, MICA, 2B4, LFA-1, or BCM1/SLAMF2, and wherein the NK cell effector agent is not IL-21.

2. The method of claim 1, wherein the composition comprises a membrane self-inserting peptide conjugated to IL-15.

3. The method of claim 1, wherein the membrane self-inserting peptide is human Fc, GPI, transmembrane T cell receptor, or pHLIP.

4. A method of expanding NK cells comprising administering to a cell population an effective amount of a composition comprising a membrane self-inserting peptide conjugated to an NK cell effector agent, wherein the cell population comprises NK cells and wherein the NK cell effector agent is selected from the group consisting of IL-15, IL-2, IL-12, IL-18, MICA, 2B4, LFA-1, or BCM1/SLAMF2, and wherein the NK cell effector agent is not IL-21.

5. The method of claim 4, wherein the composition comprises a membrane self-inserting peptide conjugated to IL 15.

6. The method of claim 4, wherein the membrane self-inserting peptide is human Fc, GPI, transmembrane T cell receptor, or pHLIP.

7. The method of claim 4, wherein administering to a cell population comprises administering the composition to a subject, wherein the subject comprises the cell population.

8. The method of claim 4, wherein the composition further comprises a second membrane self-inserting peptide conjugated to an NK cell effector agent, wherein the NK cell effector agent is selected from the group consisting of IL-15, IL-2, IL-12, IL-18, MICA, 2B4, LFA-1, or BCM1/SLAMF2.

9. The method of claim 8, wherein the two membrane self-inserting peptide conjugates are conjugated to the same or different NK cell effector agents.

10. A method of modulating the immune system comprising administering to a subject one or more of a composition comprising a membrane self-inserting peptide conjugated to an NK cell effector agent, wherein the NK cell effector agent is selected from the group consisting of IL-15, IL-2, IL-12, IL-18, MICA, 2B4, LFA-1, or BCM1/SLAMF2, and wherein the NK cell effector agent is not IL-21.

11. The method of claim 10, wherein modulating the immune system comprises reducing the number of activated T cells.

12. The method of claim 10, wherein modulating the immune system comprises expanding the number of NK cells.

13. The method of claim 10, wherein the NK cell effector agent is IL-15.

* * * * *